(12) United States Patent
Rigoutsos

(10) Patent No.: US 11,578,366 B2
(45) Date of Patent: Feb. 14, 2023

(54) COMPOSITIONS AND METHODS OF USING RNA FRAGMENTS

(71) Applicant: THOMAS JEFFERSON UNIVERSITY, Philadelphia, PA (US)

(72) Inventor: Isidore Rigoutsos, Astoria, NY (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 16/471,318

(22) PCT Filed: Dec. 22, 2017

(86) PCT No.: PCT/US2017/068261
§ 371 (c)(1),
(2) Date: Jun. 19, 2019

(87) PCT Pub. No.: WO2018/119421
PCT Pub. Date: Jun. 28, 2018

(65) Prior Publication Data
US 2020/0325537 A1    Oct. 15, 2020

Related U.S. Application Data

(60) Provisional application No. 62/498,368, filed on Dec. 22, 2016.

(51) Int. Cl.
*C12Q 1/6883* (2018.01)
*C12Q 1/686* (2018.01)

(52) U.S. Cl.
CPC ......... *C12Q 1/6883* (2013.01); *C12Q 1/686* (2013.01); *C12Q 2600/112* (2013.01); *C12Q 2600/178* (2013.01); *G01N 2800/168* (2013.01)

(58) Field of Classification Search
None
See application file for complete search history.

(56) References Cited

U.S. PATENT DOCUMENTS

2014/0235847 A1   8/2014  Sooknanan
2015/0176073 A1*  6/2015  Skog ................... C12Q 1/702
                                          506/2

FOREIGN PATENT DOCUMENTS

WO   2000027340 A2   5/2000
WO   2015153566 A1  10/2015

OTHER PUBLICATIONS

Rasmussen (Current Alzheimer Research 2015 vol. 12 984-989).*
Lambert (Non-coding RNA 2019 vol. 5 No. 16).*
Rosace (RNA Biology 2020 vol. 17, No. 8 pp. 1196-1213).*
International Search Report and Written Opinion, dated May 1, 2018, International Application No. PCT/US17/68261, 15 pages.
Love, et al., "Moderated estimation of fold change and dispersion of RNA-seq data with DESeq2", Genome Biology, 15:550 (Dec. 2014), 21 pages.

* cited by examiner

*Primary Examiner* — Amanda Haney
(74) *Attorney, Agent, or Firm* — Saul Ewing Arnstein & Lehr LLP; Kathryn Doyle; Justin Crotty

(57) ABSTRACT

The present invention includes a method for analyzing RNA fragments. In one aspect, the present invention includes a method of identifying a subject in need of therapeutic intervention to treat a disease or condition, disease recurrence, or disease progression comprises characterizing the identity of rRNA fragments. The invention also includes diagnosing, identifying or monitoring a disease or condition, and a method for identifying rRNA fragments. The invention also includes diagnosing, identifying or monitoring a glaucoma in a subject in need thereof by characterizing the identity of rRNA or tRNA fragments.

7 Claims, 17 Drawing Sheets

Specification includes a Sequence Listing.

>hg38_UsingFlankCoords_1_-_228634861_228634999_rRNA-5S_fullPlus_10_bases_BiPaddings (SEQ ID NO: 71881)

ctccttcagcGTCTACGGCCATACCACCCTGAACGCGCCCGATCTCGTCTGATCTCGGAAGCTA
AGCAGGGTCGGGCCTGGTTAGTACTTGGATGGGAGACCGCCTGGGAATACCGGGTGCTGTAGGC
Tttttctttgg

FIG. 2

>hg38_UsingFlankCoords_MT_+_638_1611_rRNA-12S_fullPlus_10_bases_BiPaddings (SEQ ID NO: 71882)

cccataaacaAATAGGTTTGGTCCTAGCCTTTCTATTAGCTCTTAGTAAGATTACACATGCAAG
CATCCCGTTCCAGTGAGTTCACCCTCTAAATCACCACGATCAAAAGGAACAAGCATCAAGCAC
GCAGCAATGCAGCTCAAAACGCTTAGCCTAGCCACACCCCACGGGAAACAGCAGTGATTAACC
TTTAGCAATAAACGAAAGTTTAACTAAGCTATACTAACCCCAGGGTTGGTCAATTTCGTGCCAG
CCACCGCGGTCACACGATTAACCCAAGTCAATAGAAGCCGGCGTAAAGAGTGTTTTAGATCACC
CCCTCCCCAATAAAGCTAAAACTCACCTGAGTTGTAAAAAACTCCAGTTGACACAAAATAGACT
ACGAAAGTGGCTTTAACATATCTGAACACACAATAGCTAAGACCCAAACTGGGATTAGATACCC
CACTATGCTTAGCCCTAAACCTCAACAGTTAAATCAACAAAACTGCTCGCCAGAACACTACGAG
CCACAGCTTAAAACTCAAAGGACCTGGCGGTGCTTCATATCCCTCTAGAGGAGCCTGTTCTGTA
ATCGATAAACCCCGATCAACCTCACCACCTCTTGCTCAGCCTATATACCGCCATCTTCAGCAAA
CCCTGATGAAGGCTACAAAGTAAGCGCAAGTACCCACGTAAAGACGTTAGGTCAAGGTGTAGCC
CATGAGGTGGCAAGAAATGGGCTACATTTTCTACCCCAGAAAACTACGATAGCCCTTATGAAAC
TTAAGGGTCGAAGGTGGATTTAGCAGTAAACTAAGAGTAGAGTGCTTAGTTGAACAGGGCCCTG
AAGCGCGTACACACCGCCCGTCACCCTCCTCAAGTATACTTCAAAGGACATTTAACTAAAACCC
CTACGCATTTATATAGAGGAGACAAGTCGTAACATGGTAAGTGTACTGGAAAGTGCACTTGGAC
GAACcagagtgtag

FIG. 3

>hg38_UsingFlankCoords_MT_+_1661_3239_rRNA-16S_fullPlus_10_bases_BiPaddings
(SEQ ID NO: 71883)

```
accgctctgaGCTAAACCTAGCCCCAAACCCACTCCACCTTACTACCAGACAACCTTAGCCAAA
CCATTTACCCAAATAAAGTATAGGCGATAGAAATTGAAACCTGGCGCAATAGATATAGTACCGC
AAGGGAAAGATGAAAAATTATAACCAAGCATAATATAGCAAGGACTAACCCCTATACCTTCTGC
ATAATGAATTAACTAGAAATAACTTTGCAAGGAGAGCCAAAGCTAAGACCCCCGAAACCAGACG
AGCTACCTAAGAACAGCTAAAAGAGCACACCCGTCTATGTAGCAAAATAGTGGGAAGATTTATA
GGTAGAGGCGACAAACCTACCGAGCCTGGTGATAGCTGGTTGTCCAAGATAGAATCTTAGTTCA
ACTTTAAATTTGCCCACAGAACCCTCTAAATCCCCTTGTAAATTTAACTGTTAGTCCAAAGAGG
AACAGCTCTTTGGACACTAGGAAAAAACCTTGTAGAGAGAGTAAAAAATTTAACACCCATAGTA
GGCCTAAAAGCAGCCACCAATTAAGAAAGCGTTCAAGCTCAACACCCACTACCTAAAAAATCCC
AAACATATAACTGAACTCCTCACACCCAATTGGACCAATCTATCACCCTATAGAAGAACTAATG
TTAGTATAAGTAACATGAAAACATTCTCCTCCGCATAAGCCTGCGTCAGATTAAAACACTGAAC
TGACAATTAACAGCCCAATATCTACAATCAACCAACAAGTCATTATTACCCTCACTGTCAACCC
AACACAGGCATGCTCATAAGGAAAGGTTAAAAAAAGTAAAAGGAACTCGGCAAATCTTACCCCG
CCTGTTTACCAAAAACATCACCTCTAGCATCACCAGTATTAGAGGCACCGCCTGCCCAGTGACA
CATGTTTAACGGCCGCGGTACCCTAACCGTGCAAAGGTAGCATAATCACTTGTTCCTTAAATAG
GGACCTGTATGAATGGCTCCACGAGGGTTCAGCTGTCTCTTACTTTTAACCAGTGAAATTGACC
TGCCCGTGAAGAGGCGGGCATAACACAGCAAGACGAGAAGACCCTATGGAGCTTTAATTTATTA
ATGCAAACAGTACCTAACAAACCCACAGGTCCTAAACTACCAAACCTGCATTAAAAATTTCGGT
TGGGGCGACCTCGGAGCAGAACCCAACCTCCGAGCAGTACATGCTAAGACTTCACCAGTCAAAG
CGAACTACTATACTCAATTGATCCAATAACTTGACCAACGGAACAAGTTACCCTAGGGATAACA
GCGCAATCCTATTCTAGAGTCCATATCAACAATAGGGTTTACGACCTCGATGTTGGATCAGGAC
ATCCCGATGGTGCAGCCGCTATTAAAGGTTCGTTTGTTCAACGATTAAAGTCCTACGTGATCTG
AGTTCAGACCGGAGTAATCCAGGTCGGTTTCTATCTACNTTCAAATTCCTCCCTGTACGAAAGG
ACAAGAGAAATAAGGCCTACTTCACAAAGCGCCTTCCCCCGTAAATGATATCATCTCAACTTAG
TATTATACCCACACCCACCCAAGAACAGGGTTTgttaagatgg
```

FIG. 4

>hg38_UsingFlankCoords_21_+_8423222_8456572_rRNA-45S_fullPlus_10000_bases_BiPaddings
(SEQ ID NO: 71884)

```
ccgccacctccctgggttcaagcgattctcctgcctcagcctcccgagtagctgggactacagg
tgcccgccaccacgcccagctaatctttatactttttaatagagacggggtttcaccgtgtcggc
ccggatggtctcgatctcttgacctcgtgacccgccgcctcggcctcccaaagtgctgggatg
acaggcgtgagccactgagcccggccttctcttgacgtttaaactatgaagtcagtccagagaa
acgcaataaatgtcaacggtgaggatggtgttgaggcagaagtaggaccacacttttcctatc
ttattcagttgataacaatatgacctaggtagtaatttcctatgtgcctacttatacacgagta
caaaagagtaaaacagagagactgctaaattaaagggtacgtgaagttcttcatagtaactccg
taaactggaacactgtcaaaaagcagcagctagtgaattgtttccatgtatttttctattatcc
aataagtgaactatgctattccttccagtctcccaagcacttcttgtccccatcaccacttcg
gtgctcgaagaaaagtaacaaatcaaggaacacaactaaagaaacacacacacaaaccaaaga
caactacagcgtctgcaaaagtttgctagaagactgaaactgttgagtataaggatctggtatt
ctacgatcatgagttcacttcagagtttgttcaagacatacgtttcgtaaggaaacatcttagt
tagaagttattcagcagtaggtaccatccctaagtattttcaccaaattcgtgacaataaaga
gctatctaaccagaaaaattagcgagtaccggcaccatccatagggctttgtctttacgcttca
ttagcacttaccatgccttacaatgtctaggattgaccctgatagcatttcgaaaacaagctaa
tgctttgtccagttcttcagtgaagacaagctcacgccctaatgcgctataggcataagcatca
tttggatccacttcgagagttctctggaagaattgaatcgcaatatcgtgttcccgttgcagac
cgaaacagttccctgcagcacaccaggcctctggctggcgaattttatccatgtctgtgaagt
ctttggacagaactgaaagagcaacctctttcggaggatgccaaagtgttgtagagtagatctc
catgccttcgactctgtaattctcaatcctcctaacctctgagaattgtctttcagcttgcgtg
gactctgaaagtttacaataggcccttccgatttggcacagtacccaaccggtattgcagtggt
gagaagctagatggctcaagatgctgatagcttctttgccgtggtaagaacacaaagctaaata
acctttccccctttcacgaagaaggctcatcaagccttccgctgctgcttttgtagattaaaa
gcctgaatctgaggcgcgattgtggctattttccttctgaaatgacggaagagtccaattttg
tcacttccaggctatcacttatgttcggtggagttattgctcctttattagttttacttttggt
tcttctgtttgggattttaggtggaaacttcattttaattttctcctattctcctcggttgtg
gagctgtcactagtcaagagtcgtgaatttcttcgaggcggtgcatttggggggagatgccatag
tggggctcaataccctgaggtgttgcccttgtcggcggaccagaactttgtgtttttgcaaggac
tggagttacctttcggctcttttcccctctgcgagaagacagacggtgttccggtttggccgatt
ctggcaacaggctttttgaaggggctccggtggatggcacgtcaatgacagacggtgtctcat
accagtgcagttttgtcaataggggtccgtctccgggacttggggtttctaatggcaaaatgcca
acacttggggttaatggactaacagctgctggtcctcctaataaacttcgaccagttttggtt
tatgttgaacctgtttagatcatatggaagttcctgttcccagtgggacagtatcaggtgaaag
gacagctgaatcgatagaagacactggggagtctgtattcaaggagtactttgaattggaagat
tctaaattccatccgtttcattcgacggtgtcctggggtgtttccgtaagaacggtctcgggct
gtctgtgacataaactaggacgaggtccaagtgttgtggcgcaacacttggacaggcagttgct
aaagctctctagagaggtgaatcaaaatgtttggtcaggatctggcttttccccctatttcac
atcatgattcaaagggacaccagaggaaaggatttcaacgaaggctcttttggtcacattctga
tcctttggtaagccgatctgtcttgcaatatacatgtcccgacgatggaagggggaagcgagct
gaatcaccaaactcaggaacgataatatcatcgtggcttttctgcttatgaaacactccacccg
ataagatttgatccccttctgcaagcttgctgagatcaacacaacatttcgcaagcaggcattt
gcattgcggggtagtacaactgtgtcctttcaagagtctatatgttttataggcctttcctgag
```

FIG. 5

```
cggtaagaacaggtcgccagtaagaacaaggcttcttctgagtgtacttctgcataaaggcgtt
ctgcgggggaaaccgcatctcggtaggcatagtggtttagtgcttgccatatagcagcctggac
gggtccctgcagcaccgccatcctcgaggctcaggcccactttctgcagtgccacaggcacccc
cccccccccatagcggctccggcccggccagcctcggctcatttaaaggcaccagccgccgtt
accggggatgggggagtccgagacagaatgacttctttatcctgctgactctggaaagcccgg
cgccttgtgatccattgcaaaccgagagtcacctcgtgtttagaacacggatccactcccaagt
tcagtgggggatgtgagggtgtggcaggtaggacgaaggactctcttccttctgattcggtc
tgcacagtggggcctaggctgggagctctctccgtgcggaccgctgactccctctaccttgggt
tccctcggccccaccctggaacgccgggccttggcagattctggcccttcctggcccttcagtc
gctgtcagaaaccccatctcatgctcggatgccccgagtgactgtggctcgcacctctccggaa
acattggaaatctctcctctacgcgcggccacctgaaaccacaggagctcgggacacacgtgct
ttcgggagagaatgctgagagtctcttgccgactctctcttgacttgagttcttcgtgggtgcg
tggttaagacgtagtgagaccagatgtattaactcaggccgggtgctggtggctcacgcctgta
acccccaacactttgggaggccgaggccgtaggatccctcgaggaatcgcctaaccctggggagg
ttgaggttgcagtgagtgagccatagttgtgtcactgtgctccagtctgggcgaaagacagaat
gaggccctgccacaggcaggcaggcaggcaggcaggcagaaagacaacagctgtattatgttct
tctcagggtaggaagcaaaaataacagaatacagcacttaattaattttttttttttcccttcgg
acggagtttcactcttggtgcccacgctggagtgcagtggcaccatctcggctcaccgcaacct
ccacctcccgcgttcaagcgattctcctgcctcagcctcctgagtagctgggattacagggagg
agccaccacacccagctgattttgtattgttagtagagacggcatttctccatgtgggtcaggc
tggtctcgaactggcgaccccagtggatctgcccgccccggcctcccaaagtgctgggtgaca
ggcgtgagccatcgtgactggccggctacgtttatttatttattttttaattattttactttt
ttttagttttccattttaatctatttatttatttacatttatttatttatttatttatttactt
atttatttattttcgagacagactctcgctctgctgcccaggctggagtgcagcggcgtgatct
cggctcactgcaagctccgcctcccgggttcacgccattctcctgcctcagcctcccaagtagc
tgggactacaggcgcccgccaccgtgcccggctaacttttgtatttgagtagagatggggtt
tcactgtggtagccaggatggtctcgatctcctgacccgtgatccgtccacctcggcctccca
aagtgctgggatgacaggcgtgagccaccgcccggcctatttatctatttattaactttgag
tccaggttatgaaaccagttagttttgtaattttttttttttttttttgagacgagg
tttcaccgtgttgccaaggcttggaccgagggatccaccggccctcggcctcccaaaagtgcgg
ggatgacaggcgcgagcctaccgcgcccggaccccccctttccccttccccgcttgtcttccc
gacagacagtttcacggcagagcgtttggctggcgtgcttaaactcattctaaatagaaatttg
ggacgtcagcttctggcctcacggactctgagccgaggagtcccctggtctgtctatcacagga
ccgtacacgtaaggaggagaaaaatcgtaacgttcaaagtcagtcatttgtgatacagaaata
cacggattcacccaaaacacagaaagcagtcttttagaaatggccttagccctggtgtccgtgc
cagtgattcttttcggtttggaccttgactgagaggattcccagtcggtctctcgtctctggac
ggaagttccagatgatccgatgggtgggggacttaggctgcgtcccccaggagccctggtcga
ttagttgtggggatcgccttggagggcgcggtgacccactgtgctgtgggagcctccatccttc
cccccacccctccccaggggatcccaattcattccgggctgacacgctcactggcaggcgtcg
ggcatcacctagcggtcactgttactctgaaaacggaggcctcacagaggaagggagcaccagg
ccgcctgcgcacagcctggggcaactgtgtcttctccaccgccccgccccacctccaagttc
ctccctccttgttgcctaggaaatcgccactttgacgaccgggtctgattgacctttgatcag
gcaaaaacgaacaaacagataaataaataaataacacaaaagtaactaactaaataaaataag
tcaatacaacccattacaatacaataagatacgatacgataggatgcgataggatacgatagga
```

FIG. 5 (Continued)

```
tacaatacaatacgatacgatacaatacaatacaatacaatacaatacaatacaatacaataca
atacaatacgccgggcgcggtggctcatgcctgtcatcccgtcactttgggatgccgaggtgga
cgcatcacctgaagtcgggagttggagacaagcccgaccaacatggagaaatcccgtctcaatt
gaaaatacaaaactagccgggcgcggtggcacatgcctataatcccagctgctaggaaggctga
ggcaggagaatcgcttgaacctgggaagcggaggttgcagtgagccgagattgcgccatcgcac
tccagtctgagcaacaagagcgaaactccgtctcaaaaataaatacataaataaatacatacat
acatacatacatacatacataaattaaaataaataaataaaataaaataaataaatgggc
cctgcgcggtggctcaagcctgtcatcccctcactttgggaggccaaggccggtggatcaagag
gcggtcagaccaacagggccagtatggtgaaacccgtctctactcacaatacacaacattagc
cgggcgctgtgctgtgctgtactgtctgtaatcccagctactcgggaggccgagctgaggcagg
agaatcgcttgaacctgggaggcggaggttgcagtgagccgagatcgcgccactgcaacccagc
ctgggcgacagagcgagactccgtctccaaaaaatgaaaatgaaaatgaaacgcaacaaaataa
ttaaaaagtgagtttctggggaaaagaagaaaagaaaaaagaaaaaaacaacaaaacagaaca
accccaccgtgacatacacgtacgcctctcgcctttcgaggcctcaaacacgttaggaattatg
cgtgatttctttttttaacttcattttatgttattatcatgattgatgtttcgagacggagtct
cggaggcccgccctccctggttgcccagacaaccccgggagacagaccctggctgggcccgatt
gttcttctccttggtcaggggtttccttgtctttcttcgtgtctttaacccgcgtggactcttc
cgctcgggtttgacagatggcagctccactttaggccttgttgttgttggggactttcctgatt
ctccccagatgtagtgaaagcaggtagatttgccttgcctggacttgcctggccttgccttttc
tttctttctttctttattactttctcttttcttcttcttcttcttcttcttcttcttcttcttcttcttcttcttctt
cttcttcttcttcttttttttttgagacagagtttcactcttgttgcccaggctagaggg
caatggtgcgatctcggctcaccgcaccctccgcctcccaggttcaagcgattctcctgcctca
gcctcctgattagctgggattacaggcatgggccaccgtgcctggctgatgtttgtacttttag
tagagacggtgttttttccatgttggtcaggctggtctcccactcccaacctcaggtggtccgcc
tgccttagcctcccaaagtgctgggatgacaggcgtgagccaccgcgcccagcctctctctctc
tctctctctctctctctctctctctctctcgctcgcttgcttgcttgctttcgtgctttctt
gctttcccgttttcttgctttctttctttctttcgtttcttcatgcttgctttcttgcttgct
tgcttgctttcgtgctttcttgctttcctgttttctttctttctttctttctttgtttctttc
ttgcttgctttcttgcttgcttgctttcgtgctttcttgttttctcgatttctttctttcttt
gtttctttcctgcttgctttcttgcttgattgctttcgtgctttcttgctttcttgttttcttt
ctttcttttgtttctttctttcttgcttccttgttttcttgctttcttgcttgcttgctttcgt
gctttcttgttttcttgctttctttcttttgtttctttcttgcttgctttcttgcttccttgtt
ttcttgctttcttgcttgcttgctttcgtgctttcttttcttgctttcttttctttctttcttt
cttttctttctttcttgctttcttttctttcattcattcattctttctttctttcctttcttt
ctttctttctttctatctttctttctttctttctttctgtttcgtccttttgagacagagtttc
actcttgtttccacggctagagtgcaatggcgcgatcttggctcaccgcaccttcgcctcccg
ggttcgagcgcttctcctgcctcagcctcccgattagcggggattacagggaggcaccccacg
cctggcttggctgatgtttgtgttttagtaggcacgccgtgtctctccatgttgctcaggctg
gtctccaactcccgacctcctgtgatgcgcccacctcggcctctcgaagtgctgggatgacggg
cgtgagccaccgtgcccggcctgttgactcatttcgcttttttatttctttcgtttccacgcgt
ttacttatatgtattaatgtaaacgtttctgtacgcttatatgcaaacaacgacaacgtgtatc
tctgcattgaatactcttgcgtatggtaaatacgtatcggttgtatggaaatagacttctgtat
gatagatgtaggtgtctgtgttatacaaataaatacacatcgctctataaagaagggatcgtcg
ataaagacgtttatttttacgtatgaaaagcgtcgtatttatgtgtgtaaatgaacgagcgtacg
```

FIG. 5 (Continued)

```
tagttatctctgttttctttcttcctctccttcgtgttttcttccttcctttcttcctttctc
tccttctttaggttttcttcctctcttcctttccttcttctctcttctgtccttttttcct
tcgtgctttatttctctttcgttccctgtgtttccttctttttcttcctctctgtttcttt
tcccttctttccttcgtttctttcctcattctttctctctttttcgtgtttctttccttcccgt
ctgtcttttaaaaatggagtgtttcagaagtttactttgtgtatctacgttttctaaattgtc
tctcttttctccattgtcttcctccctccctccctccctccctgctcccttccctccctc
cttcccttcgccatctgtctcttttccccactcccctcccccgtctgtctctgcgtggattc
cggaagagcctacccattctgcctctccgtgtgtctgcagcgacccgcgaccgagtccttgtgt
gttctttctccctccctcactccctccctccctccctgcttccgagaggcatctccaaac
acccacgcgccgtgggttgtcttctgactctgtcgcggtcgaggcagagacgcgttttgggcac
cgtttgtgtgggttggggcagaggggctgcgttttcggcctcgggaagagcttctcgactcac
ggtttcgctttcgcggtccacgggccgccctgccagccggatctgtctcgctgacgtccgcggc
ggttgtcgggctccatctggcggccgctttgagatcgtgctctcggcttccggagctgcggtgg
cagctgccgagggagggaccgtccccgctgtgagctaggcagagctccggaaagcccgcggtc
gtcagcccggctggcccggtggcgccagagctgtggcgcgtcgcttgtgagtcacagctctggc
gtgcaggtttatgtgggggagaggctgtcgctgcgcttctgggcccgcggcgggcgtggggctg
cccgggccggtcgaccagcgcgccgtagctcccgaggcccgagccgcgacccgcggggacccgc
cgcgcgtggcgcgggaggctggggacgcccttcccggcccggtcgcgggtccgcgctcatcctg
gccgtctgaggcggcggccgaattcgtttccgagtccccgtggggagccggggaccgtcccgcc
cccgtccccgggtgccggggagcggtccccgggccgggccgcggtccctctgccgcgatccttt
tctggcgagtccccgtgcggagtcggagagcgctccctgagcgcgcgtgcggcccgagaggtcg
cgcctggccggccttcggtccctcgtgtgtcccggtcgtaggaggggccggccgaaaatgcttc
cggctcccgctctggagacacgggccggccccctgcgtgtggcacgggcggccgggagggcgtc
cccggcccggcgctgctcccgcgtgtgtcctgggttgaccagagggccccgggcgctccgtgt
gtggctgcgatggtggcgttttggggacaggtgtccgtgtcgcgcgtcgcctgggccggcggc
gtggtcggtgacgcgacctcccggccccgggggaggtatatctttcgctccgagtcggcatttt
gggccgccgggttattGCTGACACGCTGTCCTCTGGCGACCTGTCGCTGGAGAGGTTGGGCCTC
CGGATGCGCGCGGGGCTCTGGCCTACCGGTGACCCGGCTAGCCGGCCGCGCTCCTGCTTGAGCC
GCCTGCCGGGGCCCGCGGGCCTGCTGTTCTCTCGCGCGTCCGAGCGTCCCGACTCCCGGTGCCG
GCCCGGGTCCGGGTCTCTGACCCACCCGGGGCGGCGGGGAAGGCGGCGAGGGCCACCGTGCCC
CCGTGCGCTCTCCGCTGCGGGCGCCCGGGGCGGCCGCGACAACCCCACCCCGCTGGCTCCGTGC
CGTGCGTGTCAGGCGTTCTCGTCTCCGCGGGGTTGTCCGCCGCCCCTTCCCCGGAGTGGGGGGT
TGGCCGGAGCCGATCGGCTCGCTGGCCGGCCGGCCGGCCTCCGCTCCCGGGGGGCTCTTCGTGA
TCGATGTGGTGACGTCGTGCTCTCCCGGGCCGGGTCCGAGCCGCGACGGGCGAGGGGCGGACGT
TCGTGGCGAACGGGACCGTCCTTCTCGCTCCGCCCCGCGGGGGTCCCCTCGTCTCTCCTCTCCC
CGCCCGCCGGCGGTGCGTGTGGGAAGGCGTGGGGTGCGGACCCCGGCCCGACCTCGCCGTCCCG
CCCGCCGCCTTCTGCGTCGCGGGCGGGCCGGCGGGTCCTCTGACGCGGCAGACAGCCCTCGC
TGTCGCCTCCAGTGGTTGTCGACTTGCGGGCGGCCCCCTCCGCGGCGGTGGGGGTGCCGTCCC
GCCGGCCCGTCGTGCTGCCCTCTCGGGGGGTTTGCGCGAGCGTCGGCTCCGCCTGGGCCCTTGC
GGTGCTCCTGGAGCGCTCCGGGTTGTCCCTCAGGTGCCCGAGGCCGAACGGTGGTGTGTCGTTC
CCGCCCCGGCGCCCCTCCTCCGGTCGCCGCCGCGGTGTCCGCGCGTGGGTCCTGAGGGAGCT
CGTCGGTGTGGGGTTCGAGGCGGTTTGAGTGAGACGAGACGAGACGCGCCCTCCCACGCGGGG
AAGGGCGCCCGCCTGCTCTCGGTGAGCGCACGTCCCGTGCTCCCCTCTGGCGGGTGCGCGCGGG
CCGTGTGAGCGATCGCGGTGGGTTCGGGCCGGTGTGACGCGTGCGCCGGCCGGCCGCCGAGGGG
```

FIG. 5 (Continued)

```
CTGCCGTTCTGCCTCCGACCGGTCGTGTGTGGGTTGACTTCGGAGGCGCTCTGCCTCGGAAGGA
AGGAGGTGGGTGGACGGGGGGGCCTGGTGGGGTTGCGCGCACGCGCGCACCGGCCGGGCCCCG
CCCTGAACGCGAACGCTCGAGGTGGCCGCGCGCAGGTGTTTCCTCGTACCGCAGGGCCCCCTCC
CTTCCCCAGGCGTCCCTCGGCGCCTCTGCGGGCCCGAGGAGGAGCGGCTGGCGGGTGGGGGGAG
TGTGACCCACCCTCGGTGAGAAAAGCCTTCTCTAGCGATCTGAGAGGCGTGCCTTGGGGGTACC
GGATCCCCCGGGCCGCCGCCTCTGTCTCTGCCTCCGTTATGGTAGCGCTGCCGTAGCGACCCGC
TCGCAGAGGACCCTCCTCCGCTTCCCCCTCGACGGGGTTGGGGGGGAGAAGCGAGGGTTCCGCC
GGCCACCGCGGTGGTGGCCGAGTGCGGCTCGTCGCCTACTGTGGCCCGCGCCTCCCCCTTCCGA
GTCGGGGGAGGATCCCGCCGGGCCGGGCCCGGCGTTCCCAGCGGGTTGGGACGCGGCGGCCGGC
GGGCGGTGGGTGTGCGCGCCCGGCGCTCTGTCCGGCGCGTGACCCCCTCCGCCGCGAGTCGGCT
CTCCGCCCGCTCCCGTGCCGAGTCGTGACCGGTGCCGACGACCGCGTTTGCGTGGCACGGGGTC
GGGCCCGCCTGGCCCTGGGAAAGCGTCCCACGGTGGGGCGCGCCGGTCTCCCGGAGCGGGACC
GGGTCGGAGGATGGACGAGAATCACGAGCGACGGTGGTGCGGGCGTGTCGGGTTCGTGGCTGCG
GTCGCTCCGGGCCCCCGGTGGCGGGGCCCCGGGGCTCGCGAGGCGGTTCTCGGTGGGGGCCGA
GGGCCGTCCGGCGTCCCAGGCGGGGCGCCGCGGGACCGCCCTCGTGTCTGTGGCGGTGGGATCC
CGCGGCCGTGTTTTCCTGGTGGCCCGGCCGTGCCTGAGGTTTCTCCCCGAGCCGCCGCCTCTGC
GGGCTCCCGGGTGCCCTTGCCCTCGCGGTCCCCGGCCCTCGCCCGTCTGTGCCCTCTTCCCCGC
CCGCCGCCCGCCGATCCTCTTCTTCCCCCCGAGCGGCTCACCGGCTTCACGTCCGTTGGTGGCC
CCGCCTGGGACCGAACCCGGCACCGCCTCGTGGGCGCCGCCGCCGGCCACTGATCGGCCCGGC
GTCCGCGTCCCCGGCGCGCGCCTTGGGGACCGGGTCGGTGGCGCCCCGCGTGGGGCCCGGTGG
GCTTCCCGGAGGGTTCCGGGGGTCGGCCTGCGGCGCGTGCGGGGGAGGAGACGGTTCCGGGGGA
CCGGCCGCGACTGCGGCGGCGGTGGTGGGGGCAGCCGCGGGGATCGCCGAGGGCCGGTCGGCCG
CCCCGGGTGCCGCGCGGTGCCGCCGGCGGCGGTGAGGCCCCGCGCGTGTGTCCCGGCCGCGGTC
GGCCGCGCTCGAGGGGTCCCCGTGGCGTCCCCTTCCCCGCCGGCCGCCTTTCTCGCGCCTTCCC
CGTCGCCCCGGCCTCGCCCGTGGTCTCTCGTCTTCTCCCGGCCCGCTCTTCCGAACCGGGTCGG
CGCGTCCCCGGGTGCGCCTCGCTTCCCGGGCCTGCCGCGGCCCTTCCCCGAGGCGTCCGTCCC
GGGCGTCGGCGTCGGGGAGAGCCCGTCCTCCCCGCGTGGCGTCGCCCCGTTCGGCGCGCGCGTG
CGCCCGAGCGCGGCCCGGTGGTCCCTGCCGGACAGGCGTTCGTGCGACGTGTGGCGTGGGTCGA
CCTCCGCCTTGCCGGTCGCTCGCCCTTTCCCGGGTCGGGGGGTGGGCCCGGGCCGGGCCTC
GGCCCCGGTCGCGGTCCCCCGTCCCGGGCGGGGCGGGCGCGCCGGCCGGCCTCGGTCGGCCCT
CCCTTGGCCGTCGTGTGGCGTGTGCCACCCCTGCGCCCGCGCCCGCCGGCGGGGCTCGGAGCCG
GGCTTCGGCCGGGCCCCGGGCCCTCGACCGGACCGGTGCGCGGCGCTGCGGCCGCACGGCGCG
ACTGTCCCCGGGCCGGGCACCGCGGTCCGCCTCTCGCTCGCCGCCCGGACGTCGGGGCCGCCCC
GCGGGGCGGGCGGAGCGCCGTCCCCGCCTCGCCGCCGCCCGCGGGCGCCGGCCGCGCGCGCG
CGCGTGGCCGCCGGTCCCTCCCGGCCGCCGGGCGCGGGTCGGGCCGTCCGCCTCCTCGCGGGCG
GGCGCGACGAAGAAGCGTCGCGGGTCTGTGGCGCGGGGCCCCGGTGGTCGTGTCGCGTGGGGGG
CGGGTGGTTGGGGCGTCCGGTTCGCCGCGCCCCGCCCCGGCCCACCGGTCCCGGCCGCCGCCC
CCGCGCCCGCTCGCTCCCTCCCGTCCGCCCGTCCGCGGCCCGTCCGTCCGTCCGTCGTCCTCCT
CGCTTGCGGGGCGCCGGGCCCGTCCTCGCGAGGCCCCCGGCCGGCCGTCCGGCCGCGTCGGGG
CCTCGCCGCGCTCTACCTTACC**TACCTGGTTGATCCTGCCAGTAGCATATGCTTGTCTCAAAGA
TTAAGCCATGCATGTCTGAGTACGCACGGCCGGTACAGTGAAACTGCGAATGGCTCATTAAATC
AGTTATGGTTCCTTTGGTCGCTCGCTCCTCTCCTACTTGGATAACTGTGGTAATTCTAGAGCTA
ATACATGCCGACGGGCGCTGACCCCCTTCGCGGGGGGATGCGTGCATTTATCAGATCAAAACC
AACCCGGTCAGCCCCTCTCCGGCCCCGGCCGGGGGCGGGCGCCGGCGGCTTTGGTGACTCTAG**
```

FIG. 5 (Continued)

```
ATAACCTCGGGCCGATCGCACGCCCCCGTGGCGGCGACGACCCATTCGAACGTCTGCCCTATC
AACTTTCGATGGTAGTCGCCGTGCCTACCATGGTGACCACGGGTGACGGGGAATCAGGGTTCGA
TTCCGGAGAGGGAGCCTGAGAAACGGCTACCACATCCAAGGAAGGCAGCAGGCGCGCAAATTAC
CCACTCCCGACCCGGGGAGGTAGTGACGAAAAATAACAATACAGGACTCTTTCGAGGCCCTGTA
ATTGGAATGAGTCCACTTTAAATCCTTTAACGAGGATCCATTGGAGGGCAAGTCTGGTGCCAGC
AGCCGCGGTAATTCCAGCTCCAATAGCGTATATTAAAGTTGCTGCAGTTAAAAAGCTCGTAGTT
GGATCTTGGGAGCGGGCGGGCGGTCCGCCGCGAGGCGAGCCACCGCCCGTCCCCGCCCCTTGCC
TCTCGGCGCCCCTCGATGCTCTTAGCTGAGTGTCCGCGGGGCCCGAAGCGTTTACTTTGAAA
AAATTAGAGTGTTCAAAGCAGGCCCGAGCCGCCTGGATACCGCAGCTAGGAATAATGGAATAGG
ACCGCGGTTCTATTTTGTTGGTTTTCGGAACTGAGGCCATGATTAAGAGGGACGGCCGGGGGCA
TTCGTATTGCGCCGCTAGAGGTGAAATTCTTGGACCGGCGCAAGACGGACCAGAGCGAAAGCAT
TTGCCAAGAATGTTTTCATTAATCAAGAACGAAAGTCGGAGGTTCGAAGACGATCAGATACCGT
CGTAGTTCCGACCATAAACGATGCCGACCGGCGATGCGGCGGCGTTATTCCCATGACCCGCCGG
GCAGCTTCCGGGAAACCAAAGTCTTTGGGTTCCGGGGGGAGTATGGTTGCAAAGCTGAAACTTA
AAGGAATTGACGGAAGGGCACCACCAGGAGTGGAGCCTGCGGCTTAATTTGACTCAACACGGGA
AACCTCACCCGGCCCGGACACGGACAGGATTGACAGATTGATAGCTCTTTCTCGATTCCGTGGG
TGGTGGTGCATGGCCGTTCTTAGTTGGTGGAGCGATTTGTCTGGTTAATTCCGATAACGAACGA
GACTCTGGCATGCTAACTAGTTACGCGACCCCCGAGCGGTCGGCGTCCCCAACTTCTTAGAGG
GACAAGTGGCGTTCAGCCACCCGAGATTGAGCAATAACAGGTCTGTGATGCCCTTAGATGTCCG
GGGCTGCACGCGCGCTACACTGACTGGCTCAGCGTGTGCCTACCCTACGCCGGCAGGCGCGGGT
AACCCGTTGAACCCCATTCGTGATGGGGATCGGGGATTGCAATTATTCCCCATGAACGAGGAAT
TCCCAGTAAGTGCGGGTCATAAGCTTGCGTTGATTAAGTCCCTGCCCTTTGTACACACCGCCCG
TCGCTACTACCGATTGGATGGTTTAGTGAGGCCCTCGGATCGGCCCCGCCGGGGTCGGCCCACG
GCCCTGGCGGAGCGCTGAGAAGACGGTCGAACTTGACTATCTAGAGGAAGTAAAAGTCGTAACA
AGGTTTCCGTAGGTGAACCTGCGGAAGGATCATTAACGGAGCCCGGAGGGCGAGGCCCGCGGCG
GCGCCGCCGCCGCGCGCTTCCCTCCGCACACCCACCCCCCACCGCGACGCGGCGCGTGCG
CGGGCGGGCCCGCGTGCCCGTTCGTTCGCTCGCTCGTTCGTTCGCCGCCCGGCCCCGCCGGCC
GCGAGAGCCGGAGAACTCGGGAGGGAGACGGGGGAGAGAGAGAGAGAGAGAGAAAGAGAAAGAA
GGGCGTGTCGTTGGTGTGCGCGTGTCGTGGGCCGGCGGGCGGCGGGGAGCGGTCCCCGGCCGC
GGCCCCGACGACGTGGGTGTCGGCGGGCGCGGGGCGGTTCTCGGCGGCGTCGCGGCGGGTCTG
GGGGGGTCTCGGTGCCCTCCTCCCCGCCGGGGCCCGTCGTCCGGCCCCGCCGCGCCGGCTCCCC
GTCTTCGGGGCCGGCCGGATTCCCGTCGCCTCCGCCGCGCCGCTCCGCGCCGCCGGGCACGGCC
CCGCTCGCTCTCCCCGGCCTTCCCGCTAGGGCGTCTCGAGGGTCGGGGCCGGACGCCGGTCCC
CTCCCCCGCCTCCTCGTCCGCCCCCGCCGTCCAGGTACCTAGCGCGTTCCGGCGCGGAGGTT
TAAAGACCCCTTGGGGGGATCGCCCGTCCGCCCGTGGGTCGGGGCGGTGGTGGGCCCGCGGGG
GAGTCCCGTCGGGAGGGCCCGGCCCCTCCCGCGCCTCCACCGCGGACTCCGCTCCCCGGCCGG
GGCCGCGCCGCCGCCGCCGCGGCGGCCGTCGGGTGGGGCTTTACCCGGCGGCCGTCGCGC
GCCTGCCGCGCGTGTGGCGTGCGCCCCGCGCCGTGGGGCGGGAACCCCGGGCGCCTGTGGGG
TGGTGTCCGCGCTCGCCCCGCGTGGGCGGCGCGCGCCTCCCCGTGGTGTGAAACCTTCCGACC
CCTCTCCGGAGTCCGGTCCCGTTTGCTGTCTCGTCTGGCCGGCCTGAGGCAACCCCCTCTCCTC
TTGGGCGGGGGGGGGGGACGTGCCGCGCCAGGAAGGGCCTCCTCCCGGTGCGTCGTCGGGAG
CGCCCTCGCCAAATCGACCTCGTACGACTCTTAGCGGTGGATCACTCGGCTCGTGCGTCGATGA
AGAACGCAGCTAGCTGCGAGAATTAATGTGAATTGCAGGACACATTGATCATCGACACTTCGAA
```

FIG. 5 (Continued)

CGCACTTGCGGCCCCGGGTTCCTCCCGGGGCTACGCCTGTCTGAGCGTCGCTTGCCGATCAATC
GCCCCCGGGGGTGCCTCCGGGCTCCTCGGGGTGCGCGGCTGGGGGTTCCCTCGCAGGGCCCGCC
GGGGGCCCTCCGTCCCCCTAAGCGCAGACCCGGCGGCGTCCGCCCTCCTCTTGCCGCCGCGCCC
GCCCCTTCCCCCTCCCCCCGCGGGCCCTGCGTGGTCACGCGTCGGGTGGCGGGGGGGAGAGGGG
GGCGCGCCCGGCTGAGAGAGACGGGGAGGGCGGCGCCGCCGCCGCCCGCGAAGACGGAGAGGGA
AAGAGAGAGCCGGCTCGGGCCGAGTTCCCGTGGCCGCCGCCTGCGGTCCGGGTTCCTCCCTCGG
GGGGCTCCCTCGCGCCGCGCGCGGCTCGGGGTTCGGGGTTCGTCGGCCCCGGCCGGGTGGAAGG
TCCCGTGCCCGTCGTCGTCGTCGTCGCGCGTCGTCGGCGGTGGGGGCGTGTTGCGTGCGGT
GTGGTGGTGGGGGAGGAGGAAGGCGGGTCCGGAAGGGGAAGGGTGCCGGCGGGGAGAGAGGGTC
GGGGGAGCGCGTCCCGGTCGCCGCGGTTCGCCGCCCGCCCCGGTGGCGGCCCGGCGTCCGGCC
GACCGCCGCTCCCGCGCCCCTCCTCCTCCCCGCCGCCCTCCTCCGAGGCCCCGCCCGTCCTCC
TCGCCCTCCCCGCGCGTACGCGCGCCCGCCCGCCCGGCTCGCCTCGCGGCGCGTCGGCCGGGGC
CGGGAGCCCGCCCCGCGGCCCGCCCGGCCGCGCCCGTGGCCGCGGCGCCGGGGTTCGCGTGTCC
CCGGCGGCGACCCGCGGGACGCCGCGGTGTCGTCCGCCGTCGCGCGCCCGCCTCCGGCTCGCGG
CCGCGCCGCGCCGCGCCGGGGCCCCGTCCCGAGCTTCCGCGTCGGGCGGGGCGGCTCCGCCGC
CGCGTCCTCGGACCCGTCCCCCCGACCTCCGCGGGGGAGACGGGTCGGGGCGTGCGGCGCCCGT
CCCGCCCCCGGCCCGTGCCCCTCCCTCCGGTCGTCCCGCTCCGGCGGGGCGGCGCGGGGGTGCC
GCCGGCCGCGCGCTCTCTCTCCCGTCGCCTCTCCCCCTCGCCGGGCCCGTCTCCCGACGGAGCG
TCGGGCGGGCGGTCGGGCCGGCGCGATTCCGTCCGTCCGTCCGCCGAGCGGCCCGTCCCCCTCC
GAGACGCGACCTCAGATCAGACGTGGCGACCCGCTGAATTTAAGCATATTAGTCAGCGGAGGAG
AAGAAACTAACCAGGATTCCCTCAGTAACGGCGAGTGAACAGGGAAGAGCCCAGCGCCGAATCC
CCGCCCCGCGGCGGGGCGCGGGACATGTGGCGTACGGAAGACCCGCTCCCCGGCGCCGCTCGTG
GGGGGCCCAAGTCCTTCTGATCGAGGCCCAGCCCGTGGACGGTGTGAGGCCGGTAGCGGCCCCC
GGCGCGCCGGGCCCGGGTCTTCCCGGAGTCGGGTTGCTTGGGAATGCAGCCCAAAGCGGGTGGT
AAACTCCATCTAAGGCTAAATACCGGCACGAGACCGATAGTCAACAAGTACCGTAAGGGAAAGT
TGAAAAGAACTTTGAAGAGAGAGTTCAAGAGGGCGTGAAACCGTTAAGAGGTAAACGGGTGGGG
TCCGCGCAGTCCGCCCGGAGGATTCAACCCGGCGGCGGGTCCGGCCGTGTCGGCGGCCCGGCGG
ATCTTTCCCGCCCCCCGTTCCTCCCGACCCCTCCACCCGCCCTCCCTTCCCCCGCCGCCCCTCC
TCCTCCTCCCCGGAGGGGGCGGGCTCCGGCGGGTGCGGGGGTGGGCGGGCGGGGCCGGGGTGG
GGTCGGCGGGGGACCGTCCCCCGACCGGCGACCGGCCGCCGCCGGGCGCATTTCCACCGCGGCG
GTGCGCCGCGACCGGCTCCGGGACGGCTGGGAAGGCCCGGCGGGGAAGGTGGCTCGGGGGGCCC
CGTCCGTCCGTCCGTCCGTCCTCCTCCTCCCCGTCTCCGCCCCCCGGCCCCGCGTCCTCCCTC
GGGAGGGCGCGCGGGTCGGGCGGCGGCGGCGGCGGCGGTGGCGGCGGCGGCGGCGGCGGCGGG
ACCGAAACCCCCCCGAGTGTTACAGCCCCCCGGCAGCAGCACTCGCCGAATCCCGGGGCCGA
GGGAGCGAGACCCGTCGCCGCGCTCTCCCCCCTCCCGGCGCCCACCCCCGCGGGGAATCCCCCG
CGAGGGGGTCTCCCCCGCGGGGGCGCGCCGGCGTCTCCTCGTGGGGGGCCGGGCCACCCCTC
CCACGGCGCGACCGCTCTCCCACCCCTCCTCCCCGCGCCCCGCCCCGGCGACGGGGGGGTGC
CGCGCGCGGGTCGGGGGCGGGGCGGACTGTCCCCAGTGCGCCCCGGGCGGGTCGCGCCGTCGG
GCCCGGGGGAGGTTCTCTCGGGGCCACGCGCGCGTCCCCCGAAGAGGGGGACGGCGGAGCGAGC
GCACGGGGTCGGCGGCGACGTCGGCTACCCACCCGACCCGTCTTGAAACACGGACCAAGGAGTC
TAACACGTGCGCGAGTCGGGGGCTCGCACGAAAGCCGCCGTGGCGCAATGAAGGTGAAGGCCGG
CGCGCTCGCCGGCCGAGGTGGGATCCCGAGGCCTCTCCAGTCCGCCGAGGGCGCACCACCGGCC
CGTCTCGCCCGCCGCGCCGGGGAGGTGGAGCACGAGCGCACGTGTTAGGACCCGAAAGATGGTG
AACTATGCCTGGGCAGGGCGAAGCCAGAGGAAACTCTGGTGGAGGTCCGTAGCGGTCCTGACGT

FIG. 5 (Continued)

```
GCAAATCGGTCGTCCGACCTGGGTATAGGGGCGAAAGACTAATCGAACCATCTAGTAGCTGGTT
CCCTCCGAAGTTTCCCTCAGGATAGCTGGCGCTCTCGCAGACCCGACGCACCCCGCCACGCAG
TTTTATCCGGTAAAGCGAATGATTAGAGGTCTTGGGGCCGAAACGATCTCAACCTATTCTCAAA
CTTTAAATGGGTAAGAAGCCCGGCTCGCTGGCGTGGAGCCGGGCGTGGAATGCGAGTGCCTAGT
GGGCCACTTTTGGTAAGCAGAACTGGCGCTGCGGGATGAACCGAACGCCGGTTAAGGCGCCCG
ATGCCGACGCTCATCAGACCCCAGAAAAGGTGTTGGTTGATATAGACAGCAGGACGGTGGCCAT
GGAAGTCGGAATCCGCTAAGGAGTGTGTAACAACTCACCTGCCGAATCAACTAGCCCTGAAAAT
GGATGGCGCTGGAGCGTCGGGCCCATACCCGGCCGTCGCCGGCAGTCGAGAGTGGACGGGAGCG
GCGGGGCGGCGCGCGCGCGCGCGTGTGGTGTGCGTCGGAGGGCGGCGGCGGCGGCGGCGGC
GGGGGTGTGGGGTCCTTCCCCCGCCCCCCCCCACGCCTCCTCCCCTCCTCCCGCCCACGCCC
CGCTCCCCGCCCCCGGAGCCCCGCGGACGCTACGCCGCGACGAGTAGGAGGGCCGCTGCGGTGA
GCCTTGAAGCCTAGGGCGCGGGCCCGGGTGGAGCCGCCGCAGGTGCAGATCTTGGTGGTAGTAG
CAAATATTCAAACGAGAACTTTGAAGGCCGAAGTGGAGAAGGGTTCCATGTGAACAGCAGTTGA
ACATGGGTCAGTCGGTCCTGAGAGATGGGCGAGCGCCGTTCCGAAGGGACGGGCGATGGCCTCC
GTTGCCCTCGGCCGATCGAAAGGGAGTCGGGTTCAGATCCCCGAATCCGGAGTGGCGGAGATGG
GCGCCGCGAGGCGTCCAGTGCGGTAACGCGACCGATCCCGGAGAAGCCGGCGGGAGCCCCGGGG
AGAGTTCTCTTTTCTTTGTGAAGGGCAGGGCGCCCTGGAATGGGTTCGCCCCGAGAGAGGGGCC
CGTGCCTTGGAAAGCGTCGCGGTTCCGGCGGCGTCCGGTGAGCTCTCGCTGGCCCTTGAAAATC
CGGGGGAGAGGGTGTAAATCTCGCGCCGGGCCGTACCCATATCCGCAGCAGGTCTCCAAGGTGA
ACAGCCTCTGGCATGTTGGAACAATGTAGGTAAGGGAAGTCGGCAAGCCGGATCCGTAACTTCG
GGATAAGGATTGGCTCTAAGGGCTGGGTCGGTCGGGCTGGGCGCGAAGCGGGGCTGGGCGCGC
GCCGCGGCTGGACGAGGCGCCGCCGCCCCCCCACGCCCGGGGCACCCCCTCGCGGCCCTCCC
CCGCCCCACCCCGCGCGCGCCGCTCGCTCCCTCCCCGCCCCGCGCCCTCTCTCTCTCTCTCC
CCCGCTCCCCGTCCTCCCCCCTCCCCGGGGGAGCGCCGCGTGGGGCGGCGGCGGGGGAGAAG
GGTCGGGGCGGCAGGGGCCGGCGGCGGCCCGCCGCGGGGCCCCGGCGGCGGGGGCACGGTCCCC
CGCGAGGGGGGCCCGGGCACCCGGGGGGCCGGCGGCGGCGGCGACTCTGGACGCGAGCCGGGCC
CTTCCCGTGGATCGCCCCAGCTGCGGCGGGCGTCGCGGCCGCCCCGGGGAGCCCGGCGGGCGC
CGGCGCGCCCCCCCCCCACCCCACGTCTCGTCGCGCGCGCGTCCGCTGGGGCGGGGAGCGGT
CGGGCGGCGGCGGTCGGCGGGCGGCGGGGCGGGGCGGTTCGTCCCCCGCCCTACCCCCCGGC
CCCGTCCGCCCCCCGTTCCCCCCTCCTCCTCGGCGCGCGGCGGCGGCGGCGGGCGGCGGAGGGG
CCGCGGGCCGGTCCCCCCGCCGGGTCCGCCCCGGGGCCGCGGTTCCGCGCGGCGCCTCGCCT
CGGCCGGCGCCTAGCAGCCGACTTAGAACTGGTGCGGACCAGGGGAATCCGACTGTTTAATTAA
AACAAAGCATCGCGAAGGCCCGCGGCGGGTGTTGACGCGATGTGATTTCTGCCCAGTGCTCTGA
ATGTCAAAGTGAAGAAATTCAATGAAGCGCGGGTAAACGGCGGGAGTAACTATGACTCTCTTAA
GGTAGCCAAATGCCTCGTCATCTAATTAGTGACGCGCATGAATGGATGAACGAGATTCCCACTG
TCCCTACCTACTATCCAGCGAAACCACAGCCAAGGGAACGGGCTTGGCGGAATCAGCGGGGAAA
GAAGACCCTGTTGAGCTTGACTCTAGTCTGGCACGGTGAAGAGACATGAGAGGTGTAGAATAAG
TGGGAGGCCCCGGCGCCCCCCGGTGTCCCGCGAGGGGCCCGGGCGGGGTCCGCCGGCCCT
GCGGGCCGCCGGTGAAATACCACTACTCTGATCGTTTTTTCACTGACCCGGTGAGGCGGGGGGG
CGAGCCCCGAGGGGCTCTCGCTTCTGGCGCCAAGCGCCCGGCCGCGCGCCGGCCGGGCGCGACC
CGCTCCGGGACAGTGCCAGGTGGGGAGTTTGACTGGGCGGTACACCTGTCAAACGGTAACGC
AGGTGTCCTAAGGCGAGCTCAGGGAGGACAGAAACCTCCCGTGGAGCAGAAGGGCAAAAGCTCG
CTTGATCTTGATTTTCAGTACGAATACAGACCGTGAAAGCGGGGCCTCACGATCCTTCTGACCT
TTTGGGTTTTAAGCAGGAGGTGTCAGAAAAGTTACCACAGGGATAACTGGCTTGTGGCGGCCAA
```

FIG. 5 (Continued)

GCGTTCATAGCGACGTCGCTTTTTGATCCTTCGATGTCGGCTCTTCCTATCATTGTGAAGCAGA
ATTCACCAAGCGTTGGATTGTTCACCCACTAATAGGGAACGTGAGCTGGGTTTAGACCGTCGTG
AGACAGGTTAGTTTTACCCTACTGATGATGTGTTGTTGCCATGGTAATCCTGCTCAGTACGAGA
GGAACCGCAGGTTCAGACATTTGGTGTATGTGCTTGGCTGAGGAGCCAATGGGGCGAAGCTACC
ATCTGTGGGATTATGACTGAACGCCTCTAAGTCAGAATCCCGCCCAGGCGGAACGATACGGCAG
CGCCGCGGAGCCTCGGTTGGCCTCGGATAGCCGGTCCCCCGCCTGTCCCCGCCGGCGGGCCGCC
CCCCCCTCCACGCGCCCCGCGCGCGCGGGAGGGCGCGTGCCCCGCCGCGCGCCGGGACCGGGGT
CCGGTGCGGAGTGCCCTTCGTCCTGGGAAACGGGGCGCGGCTGGAAAGGCGGCCGCCCCCTCGC
CCGTCACGCACCGCACGTTCGTGGGGAACCTGGCGCTAAACCATTCGTAGACGACCTGCTTCTG
GGTCGGGGTTTCGTACGTAGCAGAGCAGCTCCCTCGCTGCGATCTATTGAAAGTCAGCCCTCGA
CACAAGGGTTTGTCCGCGCGCGCGCGCGCGTGCGTGCGGGGGGCCCGGCGGGGCGTGCGCGT
CCGGCGCCGTCCGTCCTTCCGTTCGTCTTCCTCCCTCCCGGCCTCTCCCGCCGACCGCGGGCGT
GGTGGTGGGGGTGGGGGGGAGGGCGCGCGACCCCGGTCGGCGCGCCCCGCTTCTTCGGTTCCCG
CCTCCTCCCCGTTCACCGCCGGGGCGGCTCGTCCGCTCCGGGCCGGGACGGGGTCCGGGGAGCG
TGGTTTGGGAGCCGCGGAGGCGGCCGCGCCGAGCCGGGCCCGTGGCCCGCCGGTCCCCGTCCCG
GGGGTTGGCCGCGCGGGCCCCGGTGGGGCGGCCACCCGGGGTCCCGGCCCTCGCGcgtccttcc
tcctcgctcctccgcacgggtcgaccagcagaccgcgggtggtgggcggcgggcggcgaggccc
cacggggcgtccgcgcacccggccgacctccgctcgtgacctctcctcggtcgggcctccgggg
tcgaccgcctgccgcccgcgggcgtgagactcagccggcgtctcgccgtgtcccgggtcgaccg
gcgggccttctccaccgagcggcgtgtaggagtgcccgtcgggacgaaccgcaaccggagcgtc
cccgtctcggtcggcacctccggggtcgaccagctgccgcccgcgagctccggacttagccggc
gcctgcacgtgtcccgggtcgaccagcaggcggccgccggacgctgcggcgcaccgacgcgagg
gcgtcgattcccgttcgcgcgcccgcgacctccaccggcctcggcccgcggtggagctgggacc
acgcggaactccctctctcacatttttttcagccccaccgcgagtttgcgtccgcgggactttt
aagagggagtcactgctgccgtcagccagtaatgcttcctcctttttgcttttaggttttgtc
ttgcctttttttttttttttttcttctttctttctttctttctttctttctttctttctttc
tttctttctttgccgctctcgctctctcgctctctccctctctcgttttctttctctttctctt
tctctctctctctctctctctctctgtctctcgctctcgccctctctctctctctctttctc
tctgtctctctctgtctctctctctctctctctctctctctctctctctctctctctctctc
tctccctcccctccctccctctctccccttccttggtgccttctcggctcttgacacttagcc
gctgtctcgccgtgtcccgggtcgaccggcgggccttctccaccgagcggcgtgtaagagtgcc
cgtcgggacgagccggaccgccgcgtccccgtctcggtcggcacctccggggtcgaccagctg
ccgcccgcgagctccggacttagctggcgtctgcacgtgtcccgggtcgaccagcaggcggccg
ccggacgctgcggcgcaccgacgcgagggcgtcgattccggttcacgcgccggcgacctccacc
ggcctcggcccgcggtggagctgggaccacgcggaactccctcttctacatttttttcagcccc
accgcgagtttgcgtccgcgggacttttaagagggagtcactgctgccgtcagccagtaatgct
tcctcctttttgcttttaggttttgtcttgcctttttttttttttttttttttctttctttc
tttctttctttctttctttctttctttctttctttctctcgctctcgctctcgctctctc
cctcgctcgttttctttctctttctctttctctctctctctctctctctctctgtctctcgc
tctcgccctctctctctctctttctctctgtctctctctgtctctctctctctctctctctc
tctctctctctctctctctctctctccctcccctccctccctctctcccttccttg
gtgccttctcggctcttgacacttagccgctgtctcgccgtgtcccgggtcgaccggcgggcct
tctccaccgagcggcgtgtaagagtgcccgtcgggacgagccggaccgccgcgtccccgtctc
ggtcggcacctccggggtcgaccagctgccgcccgcgagctccggacttagctggcgtctgcac

FIG. 5 (Continued)

```
gtgtcccgggtcgaccagcaggcggccgccggacgctgcggcgcaccgacgcgagggcgtcgat
tccggttcacgcgccggcgacctccaccggcctcggcccgcggtggagctgggaccacgcggaa
ctccctcttctacattttttcagccccactgcgagtttgcgtccgcgggacttttaagaggga
gtcactgctgccgtcagccagtaatgcttcctccttttttgcttttggttttgccttgcgttt
tctttctttctttctttctttctttctttctttctttttctttctttctttctttctttctttct
ttctctctctctctctctctctgtctctctccctccctccctccttggtgccttctcggct
cgctgctgctgctgcctctgcctccacggttcaagcaaacagcaagttttctatttcgagtaaa
gacgtaatttcaccattttggccgggctggtctcgaactcccgacctagtgatccgcccgcctc
ggcctcccaaagactgctgggagtacagatgtgagccaccatgcccggccgattccttccttt
ttcaatcttatttttctgaacgctgccgtgtatgaacatacatctacacatacacacacacac
acacacacacacacacacacacacacacacacacacacacacccccgtagtgataaaactatg
taaatgatatttccataattaatacgtttatattatgttacttttaatggatgaatatgtatcg
aagcccccatttcatttacatacacgtgtatgtatatccttcctcccttccttcattcattattt
attaataattttcgtttatttattttcttttcttttggggccggcccgcctggtcttctgtctc
tgcgctctggtgacctcagcctcccaaatagctgggactacagggatctcttaagcccgggagg
gagaggttaacgtgggctgtgatcgcacacttccactccagcttacgtgggctgcggtggggtg
gggtgcagagaaaacgattgattgcgatctcaattgccttttagcttcattcataccctgttat
ttgctcgtttattctcatgggttcttctgtgtcattgtcacgttcatcgtttgcttgcctgctt
gcctgtttatttccttccttccttccttccttccttccttccttccttccctccttccttcctt
ccttccctcccttactggcagggtcttcctctgtctctgccgcccaggatcaccccaacctcaa
cgctttggaccgaccaaacggtcgttctgcctctgatccctcccatccccattacctgagacta
caggcgcgcaccaccacaccggctgacttttatgttgtttctcatgttttccgtaggtaggtat
gtgtgtgtgtgtgtgtgtgtgtgtgtgtgtgtgtgtgtgtgtgtgtgtatctatgtatgtatgt
atgtatgtgagtgagatgggtttcggggttctatcatgttgcccacgctggtctcgaactcctg
tcctcaagcaatccgcctgcctgcctcggccgcccacactgctgctattacaggcgtgagacgc
tgcgcctggctccttctacatttgcctgcctgcctgcctgcctgcctgcctgcctgcctgcctg
cctgcctatcaatcgtcttcttttagtacggatgtgctctcgctttattgtccatgctctggg
cacacgtggtctcttttcaaacttctatgattattattattgtaggcgtcatctcacgtgtcga
ggtgatctcgaacttttaggctccagagatcctcccgcatcggcctcccggagtgctgtgatga
cacgcgtgggcacggtacgctctggtcgtgtttgtcgtgggtcggttcttttccgttttaatac
ggggactgcgaacgaagaaaatttccagacgcatctcaccgatccgccttttcgttctttcttt
ttattctctttagacggagtttcactcttgtcgcccaggggtggagtacgatggcggctctcggc
tcaccgcaccctccgcctcccaggttcaagtgattctcctgcctcagccttcccgagtagctgg
aatgacagagatgagccatcgtgcccggctaattttctatttttactacagatggggtttctc
catcttggtcaggctggtcttcaacttccgaccgttggagaatcttaactttcttggtggtggt
tgttttccttttctttttttcttttcttttctttccttctcctccccccaccccccttg
tcgtcgtcctcctcctcctcctcctcctcctcctcctcctcctcctcctcctcctctttcattt
ctttcagctgggctctcctacgtgtgttgctctgttgctcacgctggtctcaaactcctggcct
tgacgcttctcccgtcacatccgccgtctggttgttgaaatgagcatctctcgtaaaatggaaa
agatgaaagaaataaacacgaagacggaaagcacggtgtgaacgtttctcttgccgtctcccgg
ggtgtaccttggacccggaaacacggagggagcttggctgagtgggttttcggtgccgaaacct
cccgagggcctccttccctctcccccttgtcccgcttctccccagccgaggctcccaccgcc
gccctggcattttccataggagaggtatgggagaggactgacacgccttccagatctatatcct
gccggacgtctctggctcggcgtgccccaccggctacctgccaccttccagggagctctgaggc
```

FIG. 5 (Continued)

```
ggatgcgacccccacccccccgtcacgtcccgctacccteccccggctggcctttgccgggcga
ccccaggggaaccgcgttgatgctgccttcggatcctccggcgaagacttccaccggatgcccc
gggtgggccggttgggatcagactggaccaccccggaccgtgctgttcttgggggtgggttgac
gtacagggtggactggcagccccagcattgtaaagggtgcgtgggtatggaaatgtcacctagg
atgccctccttccttcggtctgccttcagctgcctcaggcgtgaagacaacttcccatcggaa
cctcttctcttcctttctccagcacacagatgagacgcacgagagggagaaacagctcaatag
ataccgctgaccttcatttgtggaatcctcagtcatcgacacacaagacaggtgactaggcagg
gacacagatcaaacactatttccgggtcctcgtggtgggattggtctctctctctctctctctc
tctctctctctcgcacgcgcacgcgcgcacacacacacacaatttccatatctagttcacagag
cacactcacttccccttttcacagtacgcaggctgagtaaaacccgccccaccctccaccgtt
ggctgacgaaacccctctctacaattgatgaaaaagatgatctgggccgggcacgctagctca
cgcctgtcactccggcactttggaggccgaggcgggtggatcgcttggggccgggagttcgag
accaggctggccgacgtggcgaaaccccgtctctctgaaaaatagaacgattagccgggcctgg
tggcgtgggcttggaatcacgaccgctcgggagactggggcggcgacttgttccaaccgggga
ggccgaggttgcgatgagctgagatcgtgccgtggcgatgcggcctggatgacggagcgagacc
ccgtctcgagagaatcatgatgttattataagatgagttgtgcgcggtgatggccgcctgtagt
cgcggctactcgggaggctgagacgaggagaagatcacttgaggccccacaggtcgaggcttcg
gtcggccgtgacccactgtatcctgggcagtcaccggtcaaggagatatgccccttcccgttt
gcttttcttttcttcccttctcttttcttcttttttgcttctcttttcttctttctttctttct
ttctttctttcttttcttttctctcttccctcttcttcctgccttcctgcctttcttct
tttcttcttcctcccttcctcccttccttctttcctcccgcctcagcctcccaaagtgctggg
atgactggcggggaggcaccatgcctgcttggcccaaagagaccctcttggaaagtgagacgcag
agagcgccttccagtgatctcattgactgatttagagacggcatctcgctccgtcaccccggca
gtggtgccgtcgtaactcactccctgcagcgtggacgctcctggactcgagcgatccttccacc
tcagcctccagagtacagagcctgggaccgcgggcacgcgccactgtgcccacaccgtttttaa
ttgttttttttccccgagacagagtttcactctcgtggcctagactgcagtgcggtggcgcg
atcttggctcaccgcaacctctgcctcccggtttcaagcgattctcctgcatcggcctcctgag
tagccgggattgcgggcatgcgctgccacgtctggctgatttcgtattttagtggagacgggg
cttctccatgtcgatcggctggtttcgaactcccgacctcaggtgatccgccctccccggcct
ccggaagtgctgggatgacaggcgtgagccaccgcgcccggccttcatttttaaatgttttccc
acagacggggtctcatcatttctttgcaaccctcctgcccggcgtctcaaagtgctggcgtgac
gggcgtgagccactgcgcctggactccggggaatgactcacgaccaccatcgctctactgatcc
tttctttctttctttctttctttctttctttctttctttctttcttgatgaattatcttatgatttat
ttgtgtacttattttcagacggagtctcgctctgggcggggcgaggcgaggcgaggcacagcgc
atcgctttggaagccgcggcaacgcctttcaaagccccattcgtatgcacagagccttattccc
ttcctggagttggagctgatgccttccgtagccttgggcttctctccattcggaagctttgaca
ggcgcaacccacccagaggctggctgcggctgaggattagggggtgtgttggggctgaaaact
gggtcccctatttttgatacctcagccgacacatcccccgaccgccatcgcttgctcgccctct
gagatcccccgcctccaccgccttgcaggctcacctcttactttcatttcttcctttcttgcgt
ttgaggaggggtgcgggaatgagggtgtgtgtgggagggggtgcgggtggggacggagggg
agcgtcctaagggtcgatttagtgtcatgcctctttcaccaccaccaccaccgaagatgac
agcaaggatcggctaaataccgcgtgttctcatctagaagtgggaacttacagatgacagttct
tgcatgggcagaacgaggggaccggggacgcggaagtctgcttgagggaggaggggtggaagg
agagacagcttcaggaagaaaacaaaacacgaatactgtcggacacagcactgactacccgggt
```

FIG. 5 (Continued)

```
gatgaaatcatctgcacactgaacaccccgtcacaagtttacctatgtcacaatcttgcacat
gtatgcttgaacgacaaataaaagttagggggagaagagaggagagagagagagagagaga
cagagagagacagagagagagagaggagggagagagaaaacgaaacaccacctccttgacct
gagtcagggggtttctggccttttgggagaacgttcagcgacaatgcagtatttgggcccgttc
ttttttttttcttcttcttttctttcttttttttggactgagtctctctcgctctgtcacccag
gctgcggtgcggtggcgctctctcggctcactgaaacctctgcttcccgggttccagtgattct
tcttcggtagctgggattacaggcgcacaccatgacggccggctcatattcctattttcagtag
agacggggtttctccacgttggccacgctggtctcgaactcctgacctcaaatgatccgccttc
ctgggcctcccaaagtgctggaaacgacaggcctgagccgccgggatttcagcctttaaaagcg
cgggccctgccaccttttcgctgtggcccttacgctcagaatgacgtgtcctctctgccgtaggt
tgactccttgagtcccctaggccattgcactgtagcctgggcagcaagagccaaactccgtccc
ccacctccccgcgcacataataactaactaacaaactaactaactaactaaactaactaaata
aataaaatctctacacgtcacctctaagtgtgtgttcccgtgaggagtgatttctaagaaatgg
cactgtacactgaacgcagtggctcacgtctgtcatcccgaggtcaggagttcgagaccagccc
ggccaacgtggtgaaaccccgtctctactgaaaatacgaaatggagtcaggcgccgtggggca
ggcacctgtaaccccagctactcgggaggctggggtggaagaattgcttgaacctggcaggcgg
aggctgcagtgacccaagatcgcaccactgcactacagcctgggcgacagagtgagacccggtc
tccagataaatacgtacataaataaatacacacatacatacatacatacatacatacatacata
catacatacatccatgcatacagatatacaagaaagaaaaaagaaaagaaaagaaagagaaaa
tgaaagaaaaggcactgtattgctactgggctagggccttctctctgtctgtttctctctgttc
gtctctgtctttctctctgtgtctctttctctgtctgtctgtctctttctttctctctgtctct
gtctctgtctttgtctctctctctccctctctgcctgtctcactgtgtctgtcttctgtcttac
tctctttctctcccgtctgtctctctctctctctctccctccctgtttgtttctctctctccc
tccctgtctgtttctctctctctctttctgtctgtttctgtctctctctgtctgtctatgtctt
tctctgtctgtctctttctctgtctgtctgcctctctcttttcttttttctgtgtctctctgtcgg
tctctctctctctgtctgtctgtctgtctctctctctctctctctgtgcctatcttctgtctta
ctctctttctctgcctgtctgtctgtctctccctcccttttctgtttctctctctctctctct
ctctccccctctccctgtctgtttctctccgtctctctctctttctgtctgtttctcactgtct
ctctctgtccatctctctctctctgtctgtctctttcgttctctctgtctgtctgtctctct
ctctctctctctctctctctctttctgtctctcactctctgtgtgtatcttctgtcttactc
tccttctctgcctgtccgtctgtctgtctgtctgtctgtctctctctcccttctgtctctctc
tctctctgtccctctctctttctgtctgttcctctctctctctgtctctgtctttctctgtc
tgtctgcctctctctttctttctctttctgtgtctctctgtctctctctctgtgcctatcttct
gtcttactctctttctctgcctgcctgcctgtctgtctgtctgtctctctctgtctctctccct
gcctttctgtttctctctctctctccctctctctctccctctctcgctctctctgtcttctct
ctttctctctgtttctctgtctctctctgtccgtctctgtcttttctgtctgtctctctcttt
ctttctgtctgtctctgtctctgtctctctctctctctgcttgtctctctcactgtgtctgt
cctctgtcttactctccttctctgcctgtccgtctgtctgtctgtctctctctctctccctccc
tttctgtttctctctcgctctctctctctctctctctctctctctgcctgtttctctttctctc
tctgtctgtctctgtctttctctgtctgtctctttctctgtctgtctgtctccttctctctgtc
tccgtct
```

FIG. 5 (Continued)

Files listed on the CD filed with

| File Title | Reference ID |
|---|---|
| ALL_rRNA_seqs_1000GenomesProject@atleast10RPM_Population-Sex-Location_27November2016_ALL DATA | Table 10 |
| ALL_rRNA_seqs_1000GenomesProject@atleast10RPM_Population-Sex-Location_27November2016_in ≥20% of Pop-Sex-group sets | Table 11 |
| ALL_rRNA_seqs_BrainSamples@atleast1000reads_Location_27November2016_≥1000 reads in ≥1 dataset | Table 12 |
| ALL_rRNA_seqs_NormalBcells_and_CLL@atleast1000reads_Location_27November2016_≥1000 reads in ≥1 dataset | Table 13 |
| ALL_rRNA_seqs_NormalBcells_and_POAG@atleast10RPM_10December2016_xlsx_ALL DATA_PHILA-#1951575-v1-ALL_rRNA_seqs | Table 14 |
| ALL_rRNA_seqs_NormalBreast_and_TNBC@atleast10RPM_Location_27November2016_ALL DATA | Table 15 |
| ALL_rRNA_seqs_NormalBreast_and_TNBC@atleast10RPM_Location_27November2016_in ≥20% of Tissue-state sets | Table 16 |
| ALL_rRNA_seqs_PlateletSamples@atleast1000reads_Location_27November2016_≥1000 reads in ≥1 dataset | Table 17 |
| ALL_rRNA_seqs_ProstateSamples@atleast1000reads_Location_27November2016_≥1000 reads in ≥1 dataset | Table 18 |
| ALL_rRNA_seqs_TCGAProject@atleast10RPM_CancerType-Location_27November2016_ALL DATA | Table 19 |
| ALL_rRNA_seqs_TCGAProject@atleast10RPM_CancerType-Location_27November2016_in ≥20% of Cancer sets | Table 20 |
| ALL_rRNA_seqs_TCGAProject@atleast10RPM_CancerType-Location_27November2016_in ≥20% of Cancer sets-RESORTED | Table 21 |
| ALL_rRNA_seqs_POAG_exclusive_and_NOT_in_LCL_NOT_in_TCGA_NOT_inNormalandCLL_sequences_txt | Table 22 |
| ALL_NormalBcells_and_POAG_exclusive_transfer_RNA_fragments_10RPMormore_12December2016_txt | Table 23 |
| ALL_tRNA_seqs_exclusive_transfer_RNAs_10RPMormore_POAG_exclusive_and_NOT_in_LCL_NOT_in_TCGA_sequences_txt | Table 24 |

FIG. 6

| File Title | Reference ID |
|---|---|
| SAM_1000GenomesProject_CEU_vs_FIN_GBR_TSI@FDR_0_0_NegatSign | Table 25 |
| SAM_1000GenomesProject_CEU_vs_FIN_GBR_TSI@FDR_0_0_PositSign | Table 26 |
| SAM_1000GenomesProject_Men_CEU_YRI@FDR_0_0_NegatSign | Table 27 |
| SAM_1000GenomesProject_Men_CEU_YRI@FDR_0_0_PositSign | Table 28 |
| SAM_1000GenomesProject_Men_Women_CEU@FDR_0_0_NegatSign | Table 29 |
| SAM_1000GenomesProject_Men_Women_CEU@FDR_0_0_PositSign | Table 30 |
| SAM_1000GenomesProject_Men_Women_FIN@FDR_0_0_NegatSign | Table 31 |
| SAM_1000GenomesProject_Men_Women_FIN@FDR_0_0_PositSign | Table 32 |
| SAM_1000GenomesProject_Men_Women_GBR@FDR_0_0_NegatSign | Table 33 |
| SAM_1000GenomesProject_Men_Women_GBR@FDR_0_0_PositSign | Table 34 |
| SAM_1000GenomesProject_Men_Women_TSI@FDR_0_0_NegatSign | Table 35 |
| SAM_1000GenomesProject_Men_Women_TSI@FDR_0_0_PositSign | Table 36 |
| SAM_1000GenomesProject_Men_Women_YRI@FDR_0_0_NegatSign | Table 37 |
| SAM_1000GenomesProject_Men_Women_YRI@FDR_0_0_PositSign | Table 38 |
| SAM_1000GenomesProject_Women_CEU_YRI@FDR_0_0_NegatSign | Table 39 |
| SAM_1000GenomesProject_Women_CEU_YRI@FDR_0_0_PositSign | Table 40 |
| SAM_NormalBcells_and_CLL@FDR_0_0_NegatSign | Table 41 |
| SAM_NormalBcells_and_CLL@FDR_0_0_PositSign | Table 42 |
| SAM_NormalBcells_and_POAG@FDR_0_05_SAM_PositSign_txt | Table 43 |
| SAM_NormalBreast_and_TNBC@FDR_0_0_NegatSign | Table 44 |
| SAM_NormalBreast_and_TNBC@FDR_0_0_PositSign | Table 45 |
| SAM_TCGAProject_BRCA_vs_therest@FDR_0_0_NegatSign | Table 46 |
| SAM_TCGAProject_BRCA_vs_therest@FDR_0_0_PositSign | Table 47 |
| SAM_TCGAProject_PAAD_vs_therest@FDR_0_0_NegatSign | Table 48 |
| SAM_TCGAProject_PAAD_vs_therest@FDR_0_0_PositSign | Table 49 |
| SAM_TCGAProject_PRAD_vs_therest@FDR_0_0_NegatSign | Table 50 |
| SAM_TCGAProject_PRAD_vs_therest@FDR_0_0_PositSign | Table 51 |

FIG. 6 (Continued)

COMPOSITIONS AND METHODS OF USING RNA FRAGMENTS

CROSS-REFERENCE TO RELATED APPLICATIONS

The present application is a 35 U.S.C. § 371 national phase application from, and claims priority to, International Application No. PCT/US2017/068261, filed Dec. 22, 2017, and published under PCT Article 21(2) in English, which claims priority under 35 U.S.C. § 119(e) to U.S. Provisional Application No. 62/498,368, filed Dec. 22, 2016, all of which applications are incorporated herein by reference in their entireties.

BACKGROUND OF THE INVENTION

Ribosomal ribonucleic acids (rRNAs) are non-coding RNAs (ncRNAs). rRNAs are very important molecules that combine with proteins to form ribosomes. rRNAs constitute the predominant material within the ribosome, which is approximately 60% rRNA and 40% protein by weight. Within a ribosome, the rRNAs form two subunits, the large subunit (LSU) and small subunit (SSU).

Ribosomes are the complexes in which the translation from codons to amino acids occurs and protein synthesis takes place. rRNAs are present in all kingdoms of life (archaea, bacteria, and eukaryotes). Within a cell, rRNA molecules are very abundant, typically representing as much as 80% of the cell's total RNA content.

The nuclear genome of mammalian cells encodes 4 distinct types of rRNA molecules known as 5S, 5.8S, 18S and 28S, respectively. Additionally, there are two more rRNA molecules that are encoded by the mitochondrial genome and are known as 12S and 16S.

The typical nuclear genome contains many copies of the DNA template used to make rRNAs. These copies are generally organized as tandem repeats with each repeat generally comprising dozens of copies. In the human genome, hundreds of such repeats are known and can be found in several chromosomes. The only exceptions are 12S and 16S which have a single copy in the mitochondrial genome.

Three of the rRNAs that are found in the nuclear genome, namely 18S, 5.8S, and 28S, are organized as a single transcription unit that is known as 45S. Within 45S, the sequences encoding the three rRNAs are separated by 2 spacers. There are five clusters, each with 30-40 copies of 45S, on chromosomes 13, 14, 15, 21, and 22. The 45S unit is transcribed by RNA polymerase I. The 5S rRNA is transcribed by RNA polymerase III. And the 12S and 16S rRNAs are transcribed by the mitochondrial RNA polymerase gene (POLRMT).

In general, rRNA sequences are widely used for determining evolutionary relationships among organisms, since they are of ancient origin and are found in all known forms of life.

Recent reports have suggested that in other types of ncRNAs, such as transfer RNAs (tRNAs), specific fragments are functionally important for gene regulation or determining a disease state.

There is a need in the art to identify if specific fragments arise from an organism's RNA, particularly rRNA and tRNA, and to characterize the regulatory roles and functions of these RNA fragments (RFs) in diseased and healthy cells. This invention addresses this need.

SUMMARY OF THE INVENTION

The present invention relates to compositions and methods for analyzing RNA fragments.

In one aspect, the invention includes a method of identifying a subject in need of therapeutic intervention to treat a disease or condition, disease recurrence, or disease progression. The method of the invention comprises isolating fragments of rRNAs from a sample obtained from the subject; and characterizing the rRNA fragments and their relative abundance in the sample to identify a signature, wherein when the signature is indicative of a diagnosis of the disease, a treatment of the subject is recommended.

In another aspect, the invention includes a method of diagnosing, identifying or monitoring a cancer in a subject in need thereof. The method of the invention comprises isolating rRNA fragments from a cell obtained from the subject; quantifying the RNA fragments using a panel of oligonucleotides engineered to detect rRNA fragments or other method; analyzing levels of the rRNA fragments present in the cell; wherein a differential in the level of measured rRNA fragments as compared to a reference is indicative of a diagnosis or identification of a cancer in the subject; and providing a treatment regimen to the subject dependent on the differential in the level of measured rRNA fragments as compared to the reference.

In another aspect, the invention includes a method of determining the race and sex of a subject in need thereof. The method comprises isolating fragments of rRNAs from a sample obtained from the subject; characterizing the identity of the rRNA fragments and their relative abundance in the sample to identify a signature, wherein the signature is indicative of the race and sex of the subject; and recommending or providing a personalized treatment regimen or a disease prognosis to the subject based upon the subject's race and/or sex. In one embodiment, the signature indicative of the race and sex of the subject comprises at least one sequence selected from the group consisting of SEQ ID NOs: 1-28515.

In another aspect, the invention includes a method for identifying rRNA fragments comprising defining rRNA loci; sequencing a population of RNA fragments; and mapping the sequenced RNA fragments to at least one rRNA genomic loci.

In another aspect, the invention includes a kit for high-throughput analysis of rRNAs fragments in a sample from a subject in need thereof, the kit comprising a collection specially-designed qPCR assays for quantitating rRNA fragments, or panel of engineered oligonucleotides capable of hybridizing rRNA fragments, or other quantification method.

In yet another aspect, the invention includes a method of identifying a subject at risk for developing a glaucoma disorder or in need of therapeutic intervention to treat a glaucoma disorder. The method of the invention comprises isolating fragments of tRNAs from a sample obtained from the subject; and characterizing the tRNA fragments and their relative abundance in the sample to identify a signature, wherein when the signature is indicative of a prognosis for developing a glaucoma or a diagnosis for a glaucoma, a treatment of the subject is recommended.

In a further aspect, the invention includes a method of diagnosing, identifying or monitoring a glaucoma in a subject in need thereof. The method of the invention comprises isolating tRNA fragments from a cell obtained from the subject; quantitating tRNA fragments using a collection of specially-designed qPCR assays or a panel of engineered oligonucleotides capable of hybridizing tRNA fragments, or other quantification method; analyzing levels of the tRNA fragments present in the cell; wherein a differential in the level of measured tRNA fragments as compared to a reference is indicative of a diagnosis or identification of a cancer in the subject; and providing a treatment regimen to the subject dependent on the differential in the level of measured tRNA fragments as compared to the reference.

In some embodiments, the sample obtained from the subject is isolated from a cell, tissue or body fluid obtained from the subject. In some embodiments, the body fluid is selected from the group consisting of amniotic fluid, aqueous humour and vitreous humour, bile, blood serum, breast milk, cerebrospinal fluid, cerumen, chyle, chyme, endolymph and perilymph, exudates, feces, female ejaculate, gastric acid, gastric juice, lymph, mucus, pericardial fluid, peritoneal fluid, pleural fluid, pus, rheum, saliva, sebum, serous fluid, semen, smegma, sputum, synovial fluid, sweat, tears, urine, vaginal secretion, and vomit.

In some embodiments, isolating the rRNA fragments comprises isolating rRNA fragments with a length in the range of about 15 nucleotides to about 50 nucleotides.

In some embodiments, the signature indicative of a diagnosis of the disease comprises at least one sequence selected from the group consisting of SEQ ID NOs: 1-66149 and 70852-71358.

In some embodiments, characterizing the rRNA fragments comprises at least one assessment selected from the group consisting of sequencing the rRNA fragments, measuring overall abundance of one of the rRNA fragments mapped to the genome, measuring a relative abundance of the one rRNA fragment to a reference, assessing a length of the one rRNA fragment, identifying starting and ending points of the one rRNA fragment, identifying genomic origin of the one rRNA fragment, and identifying a terminal modification of the one rRNA fragment.

In some embodiments, the disease or condition, disease recurrence, or disease progression is selected from the group consisting of a cancer, a brain disease, a glaucoma and a genetically predisposed disease or condition.

In some embodiments, the cancer is selected from the group consisting of adrenocortical carcinoma, bladder urothelial carcinoma, breast invasive carcinoma, triple negative breast cancer, cervical squamous cell carcinoma and endocervical adenocarcinoma, cholangiocarcinoma, coadcolon adenocarcinoma, lymphoid neoplasm diffuse large b-cell lymphoma, esophageal carcinoma, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma and paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine corpus endometrial carcinoma, uterine carcinosarcoma, and uveal melanoma, leukemia, chronic lymphocytic leukemia, and triple negative breast cancer.

In some embodiments, the glaucoma is a primary open angle glaucoma (POAG).

In other embodiments, the signature of the POAG comprises at least one sequence selected from the group consisting of SEQ ID NOs: 65474-66149 and 70852-71358.

In some embodiments, the brain disease is Alzheimer's disease.

In some embodiments, the rRNA genomic loci comprise mitochondrial rRNA sequences from the mitochondrial genome, nuclear rRNA sequences from the nuclear genome, and mitochondria rRNA sequences from the nuclear genome.

In some embodiments, characterizing the mapped rRNA fragments comprises at least one assessment selected from the group consisting of identifying one or more of the mapped RNA fragments in a population, measuring an overall abundance of one or more of the mapped RNA fragments, measuring a relative abundance of one or more of the mapped RNA fragments to a reference, assessing a length of one or more of the mapped RNA fragments, identifying starting and ending points of one or more of the mapped RNA fragments, and identifying genomic origin of one or more of the mapped RNA fragments.

In some embodiments, isolating the tRNA fragments comprises isolating tRNA fragments with a length in the range of about 15 nucleotides to about 50 nucleotides.

In some embodiments, the tRNA signature indicative of a prognosis for developing a glaucoma or a diagnosis for a glaucoma comprises at least one sequence selected from the group consisting of SEQ ID NOs: 66150-70851 and 71359-71880.

In some embodiments, characterizing the tRNA fragments comprises at least one assessment selected from the group consisting of sequencing the tRNA fragments, measuring overall abundance of one of the tRNA fragments mapped to the genome, measuring a relative abundance of the one tRNA fragment to a reference, assessing a length of the one tRNA fragment, identifying starting and ending points of the one tRNA fragment, identifying genomic origin of the one tRNA fragment, and identifying a terminal modification of the one tRNA fragment.

In other embodiments, the tRNA or rRNA signature distinguishes a normal state as compared to disease state or condition.

In yet other embodiments, the subject is a human.

BRIEF DESCRIPTION OF THE DRAWINGS

The following detailed description of preferred embodiments of the invention will be better understood when read in conjunction with the appended drawings. For the purpose of illustrating the invention, there are examples shown in the drawings embodiments of which are presently preferred. It should be understood, however, that the invention is not limited to the precise arrangements and instrumentalities of the embodiments shown in the drawings.

FIG. 2 is a list of the nuclear 5S rRNA sequence padded on both sides with additional sequences that are aimed at accounting for any sequence reads from sequencing that might extend past the actual natural boundaries of the rRNA. The padded sequences are shown in lower case letters. The actual 5S rRNA sequence is shown in upper case letters.

FIG. 3 is a list of the mitochondrial 12S rRNA sequence padded on both sides with additional sequences that are aimed at accounting for any sequence reads from sequencing that might extend past the actual natural boundaries of the rRNA. The padded sequences are shown in lower case letters. The actual 12S rRNA sequences is shown in upper case letters.

FIG. 4 is a list of the mitochondrial 16S rRNA sequence padded on both sides with additional sequences that are aimed at accounting for any sequence reads from sequencing that might extend past the actual natural boundaries of the rRNA. The padded sequences are shown in lower case letters. The actual 16 rRNA sequence is shown in upper case letters.

FIG. 5 is a list of the nuclear 45S pre-rRNA sequence padded on both sides with additional sequences that are aimed at accounting for any sequence reads from sequencing that might extend past the actual natural boundaries of the rRNA. The padded sequences are shown in lower case letters. The actual rRNA sequences are shown in boldface upper case letters and are underlined. Nucleotides shown normal upper case letters (not underlined) correspond to spacers or to other non-rRNA sequence of the 45S pre-RNA sequence.

FIG. 6 is a table listing the name and reference identifier for 42 tables (Table 10-Table 51) located on a compact disc (CD) submitted with the U.S. Provisional Patent Application No. 62/498,368, filed Dec. 22, 2016.

DETAILED DESCRIPTION OF THE INVENTION

Figure 1:
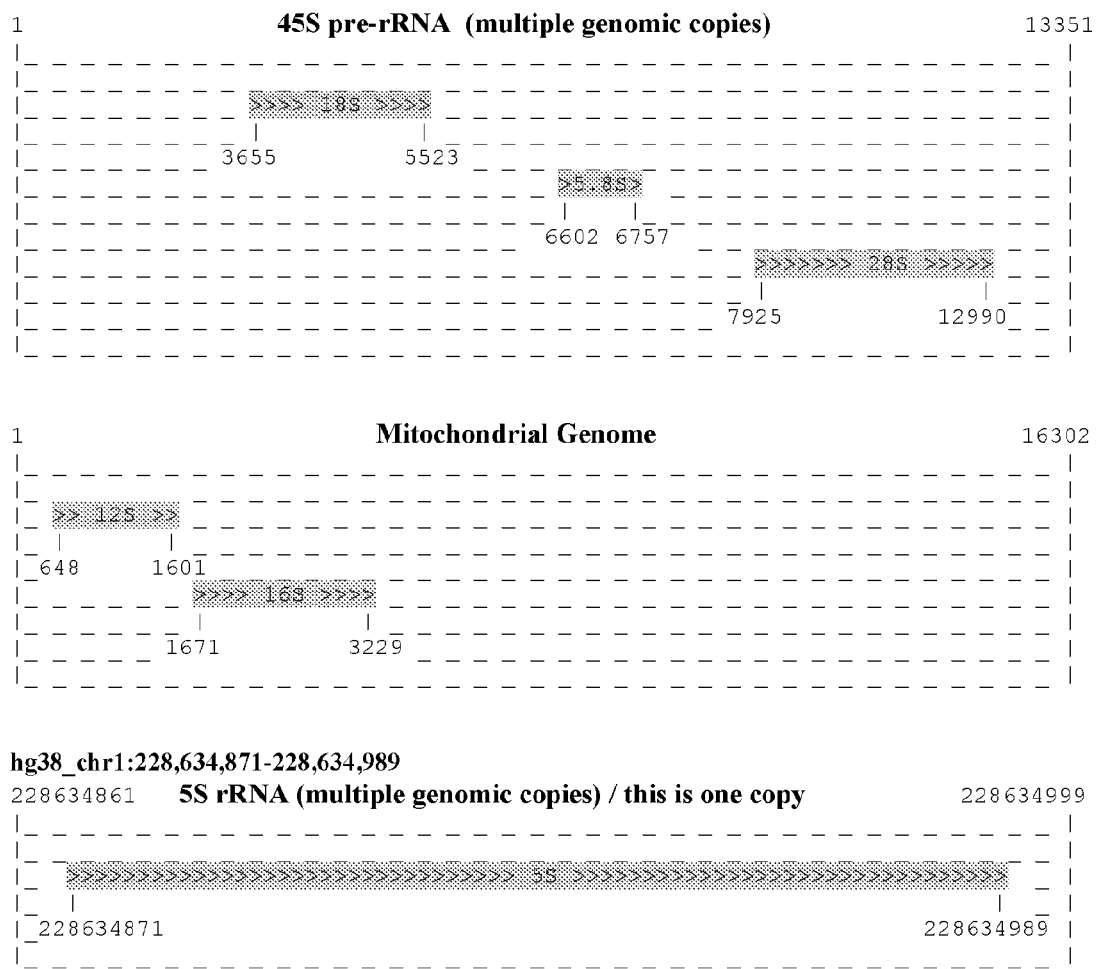
FIG. 1 is an illustration showing the genomic arrangement of the nuclear rRNA sequences: 18S, 5.8S, 28S and 5S and the mitochondrial rRNA sequences: 12S and 16S.

The full disclosures of the priority document U.S. Provisional Patent Application No. 62/231,935, filed Dec. 22, 2016, is incorporated by reference in its entireties herein.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

"About" as used herein when referring to a measurable value such as an amount, a temporal duration, and the like, is meant to encompass variations of ±20% or ±10%, more preferably ±5%, even more preferably +1%, and still more preferably ±0.1% from the specified value, as such variations are appropriate to perform the disclosed methods.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "complementary sequence" or "complement" is meant a nucleic acid base sequence that can form a double-stranded structure by matching base pairs to another polynucleotide sequence. Base pairing occurs through the formation of hydrogen bonds, which may be Watson-Crick, wooble, Hoogsteen or reversed Hoogsteen hydrogen bonding, between complementary nucleobases. For example, adenine and thymine are complementary nucleobases that pair through the formation of hydrogen bonds.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Detect" refers to identifying the presence, absence or amount of the biomarker to be detected.

The phrase "differentially present" refers to differences in the quantity and/or the frequency of a biomarker present in a sample taken from subjects having a disease as compared to a control subject. A biomarker can be differentially present in terms of quantity, frequency or both. A polypeptide or polynucleotide is differentially present between two samples if the amount or frequency of the polypeptide or polynucleotide in one sample is statistically significantly different (either higher or lower) from the amount of the polypeptide or polynucleotide in the other sample, such as reference or control samples. Alternatively or additionally, a polypeptide or polynucleotide is differentially present between two sets of samples if the amount or frequency of the polypeptide or polynucleotide in samples of the first set, such as diseased subjects' samples, is statistically significantly (either higher or lower) from the amount of the polypeptide or polynucleotide in samples of the second set, such reference or control samples. A biomarker that is present in one sample, but undetectable in another sample is differentially present.

A "disease" is a state of health of an animal wherein the animal cannot maintain homeostasis, and wherein if the disease is not ameliorated then the animal's health continues to deteriorate. A "disease subtype" is a state of health of an animal wherein animals with the disease manifest different clinical features or symptoms. For example, Alzheimer's disease includes at least three subtypes, inflammatory, non-inflammatory, and cortical.

A "disorder" as used herein, is used interchangeably with "condition," and refers to a state of health in an animal, wherein the animal is able to maintain homeostasis, but in which the animal's state of health is less favorable than it would be in the absence of the disorder. Left untreated, a disorder does not necessarily cause a further decrease in the animal's state of health.

By "effective amount" is meant the amount required to reduce or improve at least one symptom of a disease relative to an untreated patient. The effective amount of active compound(s) used to practice the present invention for therapeutic treatment of a disease varies depending upon the manner of administration, the age, body weight, and general health of the subject.

As used herein "endogenous" refers to any material from or produced inside an organism, cell, tissue or system.

The term "expression" as used herein is defined as the transcription and/or translation of a particular nucleotide sequence driven by its promoter.

By "fragment" is meant a portion of a polynucleotide or nucleic acid molecule. This portion contains, preferably, at least 10%, 20%, 30%, 40%, 50%, 60%, 70%, 80%, 90%, 91%, 92%, 93%, 94%, 95%, 96%, 97%, 98%, or 99% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. The fragment can be an autonomous and functional molecule. A fragment may contain modifications at neither, one or both of its termini. A modification can include but is not limited to a phosphate, a cyclic phosphate, a hydroxyl, and an amino acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

"Similar" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are similar at that position. The percent of similarity between two sequences is a function of the number of matching or similar positions shared by the two sequences divided by the number of positions compared X 100. For example, if 6 of 10 of the positions in two sequences are matched or similar then the two sequences are 60% similar. By way of example, the DNA sequences ATTGCC and TATGGC share 50% similarity. Generally, a comparison is made when two sequences are aligned in a way that maximizes their similarity.

As used herein, the term "inhibit" is meant to refer to a decrease in biological state. For example, the term "inhibit" may be construed to refer to the ability to negatively affect the abundance, stability, activity or localization of a ncRNA or of a protein-coding messenger RNA (mRNA) or of a protein, wherein such inhibition of the ncRNA or mRNA may result in the modulation of a gene's abundance, of a protein's mRNA abundance, of the stability of a protein's mRNA, of the transcription of a protein-coding mRNA, of the localization of a protein-coding mRNA, of the stability of a protein-coding mRNA, of the translation of a protein-coding mRNA, of the stability of a protein polypeptide, of a protein's post-translational modifications, of a protein's activity, of a protein's signaling pathway, of a ncRNA's abundance, of a ncRNA's stability, of a ncRNA's transcription, of a ncRNA's localization, of a ncRNA's post-transcriptional modifications, of a ncRNA's activity, of a ncRNA's signaling pathway, of a protein's, or any combination thereof.

"Instructional material," as that term is used herein, includes a publication, a recording, a diagram, or any other medium of expression that may be used to communicate the usefulness of the compounds of the invention. In some instances, the instructional material may be part of a kit useful for effecting alleviating or treating the various diseases or conditions recited herein. Optionally, or alternately, the instructional material may describe one or more methods of alleviating the diseases or conditions in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "mitochondrial rRNAs" is used to refer to ribosomal RNAs encoded in the mitochondrial genome. The term "nuclear rRNAs" is used to refer to ribosomal RNAs encoded in the nuclear genome.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By "isolated polynucleotide" is meant a nucleic acid (e.g., a DNA or an RNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a rRNA, cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

The term "oligonucleotide panel" or "panel of oligonucleotides" refers to a collection of one or more oligonucleotides that may be used to identify DNA (e.g. genomic segments comprising a specific sequence, DNA sequences bound by particular protein, etc.) or RNA (e.g. mRNAs, microRNAs, tRNAs, rRNAs etc.) or fragments thereof through hybridization of complementary regions between the oligonucleotides and the DNA or RNA. If the sought molecule is RNA, it is commonly converted to DNA through a reverse transcription step). The oligonucleotides may include complementary sequences to known DNA or known RNA sequences. The oligonucleotides may be engineered to be between about 5 nucleotides to about 40 nucleotides, or about 5 nucleotides to about 30 nucleotides, or about 5 nucleotides to about 20 nucleotides, or about 5 nucleotides to about 15 nucleotides in length. The term "oligonucleotide panel" or "panel of oligonucleotides" could also refer to a system and accompanying collection of reagents that, in addition to being able to hybridize to molecules containing a complementary sequence, can also ensure that the identified molecule's 3' terminus matches precisely the 3' terminus of the sought molecule, or that the identified molecule's 5' terminus matches precisely the 5' terminus of the sought molecule, or both: this ability is unlike what can be achieved by conventional assays such as e.g. Affymetrix chips and methods (e.g. "dumbbell-PCR") and systems (e.g. the Fireplex system of Firefly BioWorks) that can achieve this are now beginning to be available.

The term "operably linked" refers to functional linkage between a regulatory sequence and a heterologous nucleic acid sequence resulting in expression or changes in abundance of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormally high level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art. The term "underexpressed" tumor antigen or "underexpression" of the tumor antigen is completely analogous.

The term "overexpressed" tumor promoter or "overexpression" of the tumor promoter is intended to indicate an abnormally high level of expression of the tumor promoter RNA or protein in a cell from a disease area like a solid tumor within a specific tissue or organ of the patient relative to the level of expression in a normal cell from that tissue or organ. Patients having solid tumors or a hematological malignancy characterized by overexpression of the tumor promoter can be determined by standard assays known in the art. The term "underexpressed" tumor promoter or "underexpression" of the tumor promoter is completely analogous.

The term "overexpressed" tumor suppressor or "overexpression" of the tumor suppressor is intended to indicate an abnormally high level of abundance of the tumor suppressor RNA or protein in a cell from a specific area within a specific tissue or organ of an individual relative to the level of abundance under typical circumstances in a cell from that tissue or organ. Individuals having characteristic overexpression of the tumor suppressor can be determined by standard assays known in the art. The term "underexpressed" tumor suppressor or "underexpression" of the tumor suppressor is completely analogous.

The terms "patient," "subject," "individual," and the like are used interchangeably herein, and refer to a human or non-human mammal, or cells thereof whether in vitro or in situ, amenable to the methods described herein. Non-human mammals include, for example, livestock and pets, such as ovine, bovine, porcine, canine, feline and murine mammals. The term "subject" is intended to include living organisms in which an immune response can be elicited (e.g., mammals). Examples of subjects include humans, dogs, cats, mice, rats, and transgenic species thereof. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which may be hydrolyzed into the monomeric "nucleotides." The monomeric nucleotides may be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means. The following abbreviations for the commonly occurring nucleic acid bases are used. "A" refers to adenosine, "C" refers to cytosine, "G" refers to guanosine, "T" refers to thymidine, and "U" refers to uridine. The term "RNA" as used herein is defined as ribonucleic acid. The term "recombinant DNA" as used herein is defined as DNA produced by joining pieces of DNA from different sources.

As used herein, the terms "prevent," "preventing," "prevention," and the like refer to reducing the probability of developing a disease or condition in a subject, who does not have, but is at risk of or susceptible to developing a disease or condition.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The terms "purified," or "biologically pure" refer to material that is free to varying degrees from components which normally accompany it as found in its native state. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "race" refers to a taxonomic rank below the species level, a collection of genetically differentiated human populations defined by phenotype. White (Wh) is the National Health Institute/The Cancer Genome Atlas (NIH/TCGA) designation for a person with origins in any of the original peoples of the far Europe, the Middle East, or North Africa. Black or African American (B/Aa) is the NIH/TCGA designation for a person with origins in any of the black racial groups of Africa.

By "reduces" or "decreases" is meant a negative alteration of at least 10%, 25%, 50%, 75%, or 100%.

By "reference" is meant a standard or control. A "reference" is also a defined standard or control used as a basis for comparison.

As used herein, "relative abundance" refers to the ratio of the quantities of two or more molecules of interest (e.g. rRNAs, rRNA fragments, tRNAs, tRNA fragments, miRNAs, etc.) present in a sample. The relative abundance of two or more molecules of interest in a given sample may differ from the relative abundance of the same two or more molecules in a second sample.

The terms "rRNA fragment" or "rRF" are all used to refer to short non-coding RNAs generated from a rRNA locus. rRNA fragments have lengths that range from 10 to 50 or more nucleotides.

The terms "tRNA fragment" or "tRF" are all used to refer to short non-coding RNAs generated from a tRNA locus. tRNA fragments have lengths that range from 10 to 50 or more nucleotides.

As used herein, "sample" or "biological sample" refers to anything, which may contain the biomarker (e.g., polypeptide, polynucleotide, or fragment thereof) for which a biomarker assay is desired. The sample may be a biological sample, such as a biological fluid or a biological tissue or an isolated cell or a collection of isolated cells. In one embodiment, a biological sample is a tissue sample including pulmonary vascular cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

As used herein, the term "سensitivity" is the percentage of biomarker-detected subjects with a particular disease.

As used herein, "sample" or "biological sample" refers to anything, which may contain the biomarker (e.g., polypeptide, polynucleotide, or fragment thereof) for which a biomarker assay is desired. The sample may be a biological sample, such as a biological fluid or a biological tissue. In one embodiment, a biological sample is a tissue sample including pulmonary vascular cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

As used herein, the term "sensitivity" is the percentage of biomarker-detected subjects with a particular disease.

The terms "short RNA profile" or "RNA profile" or "rRNA profile" or "rRNA fragment profile" or "tRNA profile" or "tRNA fragment profile" are used interchangeably and refer to a genetic makeup of RNA molecules that are present in a sample, such as a cell, tissue, or subject. Optionally, the abundance of an RNA molecule that is part of an RNA profile may also be sought. Optionally, other attributes of an RNA molecule that is part of an RNA profile may also be sought and include but are not limited to a molecule's location within the genomic locus of origin, the molecule's starting point, the molecule's ending point, the molecule's length, the identity of the molecule's terminal modifications, etc. The RNA molecules that can be used to form such a profile can be miRNAs, miRNA isoforms, mRNAs, rRNAs, rRNA fragments, tRNAs, tRNA fragments, etc. as well as combinations thereof.

The term "signature" or "RNA signature" as used herein refers to a subset of an RNA profile and comprises the identity of one or more molecules that are selected from an RNA profile and optionally one or more of the attributes of the one or more molecules that are selected from the RNA profile.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison. The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disease or condition being treated. The therapeutically effective amount will vary depending on the compound, the disease and its severity and the age, weight, etc., of the subject to be treated.

The term "therapeutic" as used herein means a treatment and/or prophylaxis. A therapeutic effect is obtained by suppression, remission, or eradication of a disease state. As used herein, the terms "treat," treating," "treatment," and the like refer to reducing or improving a disease or condition and/or symptom associated therewith. It will be appreciated that, although not precluded, treating a disease or condition does not require that the disease, condition or symptoms associated therewith be completely ameliorated or eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DESCRIPTION

The present invention includes methods and compositions of analyzing RNA fragments (i.e rRNA and tRNA Fragments).

rRNAs and tRNAs are ancient non-coding RNAs (ncR-NAs). As such, rRNAs and tRNAs are present in archaea, bacteria, and eukaryotes. rRNAs are key molecules in cells. Described herein, rRNA and tRNA loci produce fragments that are important for characterizing race, sex, age, disease prognosis, disease diagnosis, etc. The present invention utilizes rRNA and tRNA fragments profiling to identify subjects in need of therapeutic intervention.

In one aspect, the invention provides a method of identifying a subject in need of therapeutic intervention to treat a disease, disease progression, or disease recurrence. The method comprises isolating fragments of rRNAs or tRNAs from a sample obtained from the subject; characterizing the fragments of rRNAs or tRNAs and their relative abundance in the sample to identify a signature, wherein when the signature is indicative of a diagnosis of the disease (or of a disease subtype or of a disease recurrence), a treatment of the subject is recommended or provided. The recommended treatment may be personalized and depend on the subject's attributes. In one embodiment, these attributes may include the subject's sex, or the subject's race, or the subject's age, or a combination thereof. As such, it may be necessary to further characterize the fragments of rRNAs or tRNAs and their relative abundance in the sample to identify a signature, wherein when the signature can inform the subject's physician of the subject's sex, or race, or age and weigh in on the recommended or provided treatment.

In another aspect, a method of identifying a sample's tissue of origin to treat a disease or disease progression or disease recurrence in a subject is provided. In one embodiment the sample is a metastatic sample. The method comprises isolating RNA fragments (RFs) from a sample obtained from the subject; characterizing the identity of the RFs and their relative abundance in the samples to identify a signature, wherein the signature is indicative of the sample's tissue of origin, or the disease status of the tissue of origin; and recommending or providing a personalized treatment regimen or a disease prognosis to the subject dependent on the sample's tissue of origin, or the disease status of the tissue of origin, or the subject's sex, race or age.

rRNA/tRNA Fragments

Analysis of RNA fragment profiles or signatures in one or more cells can lead to the discovery of RNA signatures present in healthy cells or diseased cells. RNA signatures of one or more cells, or a tissue may be used to identify a diseased cell, disease progression, or disease recurrence in a subject. Thus, the subject may be identified as in need of therapeutic intervention to delay the onset of, reduce, improve, and/or treat a disease or condition, such as cancer, in a subject in need thereof.

In another aspect, the invention includes a method for identifying rRNA or tRNA fragments from sequenced reads, typically obtained through next generation sequencing approaches.

Various sequencing methodologies and platforms are known in the art. The choice of a platform may be based on the user's and experiment's requirements. In some embodiments, the sequencing method is a high throughput next-generation method. Non limiting, examples of massively parallel signature sequencing platforms are Illumina sequencing by synthesis (Illumina, san Diego Calif.), 454 pyrosequencing (Roche Diagnostics, Indianapolis Ind.), SOLiD sequencing (Life Technologies, Carlsbad, Calif.), Ion Torrent semiconductor sequencing (Life Technologies, Carlsbad, Calif.), Heliscope single molecule sequencing (Helicon Biosciences, Cambridge, Mass.), and Single molecule real time (SMRT) sequencing (Pacific Biosciences, Menlo Park, Calif.).

The method for identifying rRNA fragments of this invention comprises the steps of defining rRNA loci; mapping the sequenced reads to at least one rRNA or tRNA genomic locus comprising disregarding map locations that differ from the rRNA fragments by at least an insertion, deletion, or replacement of a nucleotide, optionally excluding rRNA or tRNA fragments that map to locations outside of the known rRNA or tRNA loci; mapping sequenced reads that may have been post-transcriptionally modified; and characterizing the remaining sequenced reads.

The human nuclear and human mitochondrial genomes comprise many rRNAs. It is known in the art that rRNA loci include the mitochondrial genome loci of mitochondrial rRNA sequences, and the nuclear genome loci of nuclear rRNA sequences. The nuclear genome also includes loci whose sequences resemble mitochondrial rRNA sequences.

The sequenced reads are further mapped to at least one rRNA genomic locus. Sequenced reads that differ from the map location by at least an insertion, deletion, or replacement of a nucleotide are optionally disregarded. Sequenced reads that map outside rRNA loci are optionally discarded to avoid erroneous results. Sequences reads that map inside rRNA loci (e.g. the 45S pre-rRNA) but outside the confines of rRNAs (e.g. in the spacers separating the rRNAs or in the sequence preceding the 18S rRNA or in the sequence following the 28S rRNA) may be optionally retained as they can improve the quality of the signature.

The identified RNA fragments of the invention (i.e. rRFs and/or tRFs) can be further assessed for one or more of, sequence of the RNA fragments, the overall abundance of the RNA fragments based on the number of sequenced reads that mapped to RNA loci, the relative abundance of an RNA fragment to a reference, the relative abundance of two RNA fragments with respect one another, the terminal modifications of an RNA fragment, the length of an RNA fragment, the starting and ending points of a RNA fragment, the genomic origin of an RNA fragment, and other analyses known in the art.

Also provided in this invention is a panel of engineered oligonucleotides comprising a mixture of oligonucleotides capable of hybridizing to RNA fragments. In some embodiments, these engineered oligonucleotides are about 5 to about 15 nucleotides (nts) in length and capable of hybridizing rRNA fragments and/or rRNAs, wherein the rRNA fragments are generally at least 15 nts in length and generally less than 60 nts in length. The panel may include one or more oligonucleotides that may be used to identify rRNA fragments or rRNAs through hybridization of complementary regions between the oligonucleotides and the rRNAs, or related techniques that are well known to those skilled in the art. The oligonucleotides may include complementary sequences to known rRNA sequences, such as rRNA fragments. The oligonucleotides may be engineered to be between about 5 nucleotides to about 40 nucleotides, or about 5 nucleotides to about 30 nucleotides, or about 5 nucleotides to about 20 nucleotides, or about 5 nucleotides to about 15 nucleotides in length. The panel may include engineered oligonucleotides that are specific to a cell type, tissue of interest, disease type, disease subtype, stage of disease, a patient's sex, a patient's population of origin, a patient's race or other aspect that may differentiate rRNA fragment signatures. The kits and oligonucleotide panel may also be used to identify agents that modulate disease, or progression of disease, or disease recurrence, in patient samples, and/or in in vitro or in vivo animal models for the disease at hand.

Alternate methods for quantifying the abundance levels of a select collection of ncRNAs that comprise the signature of interest, particularly rRNAs or tRNAs and/or rRNA or tRNAs fragments include: a set of specially designed TaqMan® assays, classical TaqMan® Gene Expression Assays, TaqMan® Low Density Array-micro fluidic cards (Applied Biosystems/Thermo-Fisher Scientific); a set of end-point specific assays such as dumbbell-PCR; a set of miR-ID assays (Somagenics, Inc.); or, other quantitative PCR (qPCR) systems known in the art.

The abundance levels of the ncRNAs that comprise the signature of interest, particularly rRNAs, tRNAs and/or rRFs or tRFs, may also be measured by other technologies known in the art, e.g. deep-sequencing technologies."

Diagnostics

Samples from subjects suffering from a disease or a condition have a specific rRNA fragment profile in the cell or cells that are diseased, including metastatic cancer cells. In other instances, the disease or a condition can affect the expression patterns of mRNAs and ncRNAs, including rRNAs, tRNAs, and miRNAs, in other cells or cell types that need not be part of the organ that is primarily associated with the disease or condition. In such cases, the sample need not originate from the organ and alternative sources of material can be used instead for examining a signature of interest.

Identifying the cellular origin or tissue origin of a cancer metastasis, or a propensity for a cell to metastasize by identifying a rRNA fragment profile associated with the cellular origin or tissue origin or a propensity to metastasize in a sample obtained from the subject allows recommending or offering the subject a personalized treatment. In one aspect, the invention includes a method of identifying a cell's tissue of origin to treat a disease or disease progression, or disease recurrence in a subject in need thereof comprising isolating fragments of rRNAs (or tRNAs) from a sample (e.g. a cell) obtained from the subject; characterizing the fragments of rRNA (or tRNA), which can include assessing one or more of, overall abundance, relative abundance, length of the fragment, starting and ending points of the fragment, terminal modifications, etc., in the sample to identify a signature, wherein the signature is indicative of the cell's tissue of origin, and/or disease status of the tissue of origin; and providing a treatment regimen to the subject dependent on the cell's tissue of origin and/or disease status of the tissue of origin.

Identifying the existence of a disease or condition by identifying a rRNA fragment profile associated with the disease or condition in a sample obtained from the subject allows recommending or offering the subject a personalized treatment. In one aspect, the invention includes a method of identifying a cell's rRNA fragment population to establish and treat the onset of a disease, or the state of the disease, or that disease has recurred in a subject in need thereof comprising isolating fragments of rRNAs from a sample (e.g. a cell) obtained from the subject; characterizing the fragments of rRNA, which can include assessing one or more of, overall abundance, relative abundance, length of the fragment, starting and ending points of the fragment, terminal modifications, etc., in the sample to identify a signature, wherein the signature is indicative of the presence of the disease, of the state of the disease, or of disease recurrence; and providing a treatment regimen to the subject dependent on the sampled cell's profile of rRNAs.

In another embodiment, characterizing the rRNA fragments that are present in the RNA profile can identify subjects in need of treatment.

In another embodiment, analyzing the length of rRNA fragments in a cell, tissue or body fluid is used to identify subjects in need of treatment. In another embodiment, analyzing the length of rRNA fragments in cell, tissue or body fluid is used to identify subjects with a disease subtype.

In yet another embodiment, the relative abundance of the RNA fragments that are present in the RNA profile can identify subjects in need of treatment. In another approach, diagnostic methods are used to assess RNA fragment profiles in a biological sample relative to a reference (e.g., rRNA fragment profile in a healthy cell or tissue or body fluid in a corresponding control sample). Examples of a body fluid may include, but are not limited to, amniotic fluid, aqueous humour and vitreous humour, bile, blood serum, breast milk, cerebrospinal fluid, cerumen, chyle, chyme, endolymph and perilymph, exudates, feces, female ejaculate, gastric acid, gastric juice, lymph, mucus, pericardial fluid, peritoneal fluid, pleural fluid, pus, rheum, saliva, sebum, serous fluid, semen, smegma, sputum, synovial fluid, sweat, tears, urine, vaginal secretion, and vomit.

In one embodiment, the sample, such as a cell or tissue or body fluid is obtained from the subject. In another embodiment, the cell or tissue or body fluid is isolated from the sample. In another embodiment, the cell or tissue is isolated from a body fluid. The sample may be a peripheral blood cell, a tumor cell, a circulating tumor cell, an exosome, a bone marrow cell, a breast cell, a lung cell, a pancreatic cell, or other cell of the body.

In another embodiment, a signature of rRNA (or tRNA) fragments or a presence or absence of specific rRNA (or tRNA) fragments are indicative a diagnosis of a disease or condition. In some embodiments, the signature of rRNA fragments distinguishes a normal state as compared to a disease state or a condition.

In one embodiment, the signature of rRNA fragment comprises at least one sequence listed in at least one table selected from the group consisting of: Tables 10-22, 52 and 53. In another embodiment, the signature of rRNA fragment comprises at least one sequence selected from the group consisting of SEQ ID NOs: 1-66149 and 70852-71358.

In a particular embodiment, the methods or assays described herein can comprise analyzing the presence or absence or the signature of RNA fragments in a disease or condition, disease recurrence, or disease progression selected from the group consisting of a cancer, a brain disease, a glaucoma, or a genetically predisposed disease or condition.

In one embodiment, the cancer is selected from the group consisting of adrenocortical carcinoma, bladder urothelial carcinoma, breast invasive carcinoma, triple negative breast cancer, cervical squamous cell carcinoma and endocervical adenocarcinoma, cholangiocarcinoma, coad-colon adenocarcinoma, lymphoid neoplasm diffuse large b-cell lymphoma, esophageal carcinoma, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma and paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine corpus endometrial carcinoma, uterine carcinosarcoma, and uveal melanoma, leukemia, and chronic lymphocytic leukemia.

In another embodiment, the cancer is the subtype of breast cancer known as "triple negative."

In another embodiment, the cancer is chronic lymphocytic leukemia.

In another embodiment, the brain disease is Alzheimer's disease.

In another embodiment, the glaucoma is an open angle glaucoma.

In yet another embodiment, the methods or assays described herein can comprise detecting the presence or absence of one or more RNA fragments to distinguish B-cells between subjects of different race such as but not limited to B-cells from white people from B-cells from black people. Such an assessment may assist in offering or providing optimal personalized treatment.

In yet another embodiment, the methods or assays described herein can comprise detecting the presence or absence of one or more rRNA fragments to distinguish platelets from people with a propensity to clot or hemorrhage as listed in Table 17 (SEQ ID NOs: 62836-62914).

In yet another embodiment, the methods or assays described herein can comprise detecting rRNA fragments as signature for POAG, wherein the rRFs signature comprises at least one sequence selected from the group consisting of SEQ ID NOs: 65474-66149 and 70852-71358.

Measuring the abundance of fragments from transfer RNAs (tRNAs) also known as tRFs in a subject, or a sample from a subject, is also included in the invention. It is now known in the literature that tRFs are produced constitutively through fragmentation of precursor and mature tRNAs. In one embodiment, the invention includes a method of identifying a subject at risk for developing a glaucoma disorder or in need of therapeutic intervention to treat a glaucoma disorder. The method of the invention comprises isolating fragments of tRNAs from a sample obtained from the subject; and characterizing the tRNA fragments and their relative abundance in the sample to identify a signature, wherein when the signature is indicative of a prognosis for developing a glaucoma or a diagnosis for a glaucoma, a treatment of the subject is recommended. In some embodiments, characterizing the tRNA fragments comprises at least one assessment selected from the group consisting of sequencing the tRNA fragments, measuring overall abundance of one of the tRNA fragments mapped to the genome, measuring a relative abundance of the one tRNA fragment to a reference, assessing a length of the one tRNA fragment, identifying starting and ending points of the one tRNA fragment, identifying genomic origin of the one tRNA fragment, and identifying a terminal modification of the one tRNA fragment.

In another embodiment, the invention includes a method of diagnosing, identifying or monitoring a glaucoma in a subject in need thereof. The method comprises isolating tRNA fragments from a cell obtained from the subject; hybridizing the tRNA fragments to a panel of oligonucleotides engineered to detect tRNA fragments; analyzing levels of the tRNA fragments present in the cell; wherein a differential in the level of measured tRNA fragments as compared to a reference is indicative of a diagnosis or identification of a cancer in the subject; and providing a treatment regimen to the subject dependent on the differential in the level of measured tRNA fragments as compared to the reference.

In one embodiment, the signature of tRNA fragment comprises at least one sequence listed in at least one table selected from the group consisting of: Tables 23, 24, 54 and 55. In another embodiment, the signature of rRNA fragment comprises at least one sequence selected from the group consisting of SEQ ID NOs: 66150-70851 and 71359-71880.

In general, characterizing the rRNA or tRNA fragments of this invention identifies a signature that may be indicative of a diagnosis of a disease or condition, the onset of a disease or condition, or the recurrence of a disease or condition. The character of the rRNA or tRNA fragments in the sample may be compared with a reference, such as other rRNAs or tRNA present within the cell, a healthy cell or a diseased cell will yield a relative abundance of the rRNA or tRNA fragments to identify a signature. Alternatively, the abundance of two or more rRNA/rRNA fragments, two or more tRNAs/tRNA fragments, or at least one rRNA/rRNA fragment and at least one tRNA/tRNA fragment may be compared to identify a signature. Alternatively, the signature may be established by comparing the rRNA or tRNA fragments' locations within the genomic loci of origin, the starting and ending points of the fragments, the length of the fragment, and any other feature of the fragments as compared to other rRNA or tRNA fragments within the same sample or another sample or reference to distinguish a diseased state or condition, a propensity to develop a disease or condition, and/or the absence of a disease or condition. The skilled artisan will appreciate that the diagnostic can be adjusted to increase sensitivity or specificity of the assay. In general, any significant increase (e.g., at least about 10%, 15%, 30%, 50%, 60%, 75%, 80%, or 90%) in the level of a polynucleotide or polypeptide biomarker in the subject sample relative to a reference may be used to diagnose a diseased state, a propensity to develop a disease or condition, and/or the absence of a disease or condition.

Accordingly, an rRNA or tRNA fragment profile may be obtained from a sample from a subject and compared to a reference rRNA or tRNA fragment profile obtained from a reference cell or tissue or body fluid, so that it is possible to classify the subject as belonging to or not belonging to the reference population. The association may take into account the presence or absence of one or more rRNA or tRNA fragments in a test sample and the frequency of detection of the rRNA or tRNA fragments in a test sample compared to a control. The association may take into account both of such factors to facilitate a diagnosis of a disease or condition. The association may take into account both of such factors to guide recommending or offering a treatment. In one embodiment, the reference is the identity and abundance level of the rRNA or tRNA fragments present in a control sample, such as non-diseased cell, a cell obtained from a patient that does not have the disease or condition at issue or a propensity to develop such a disease or condition. In another embodiment, the reference is a baseline level of the rRNA or tRNA fragment presence and abundance in a biologic sample derived from the patient prior to, during, or after treatment for the disease or condition. In yet another embodiment, the reference is a standardized curve.

Methods of Use

In one aspect, the invention includes a method of identifying the race or sex of a subject in need of treatment. The method comprises isolating fragments of rRNAs from a sample obtained from the subject; characterizing the identity of the rRNA fragments and their relative abundance in the sample to identify a signature, wherein the signature is indicative of the race and sex of the subject; and recommending or providing a personalized treatment regimen or a disease prognosis to the subject based upon its race and sex. In some embodiments, the signature comprises at least one sequence listed in at least one table selected from the group consisting of Table 10, and Table 11 (SEQ ID NOs: 1-28515).

In another aspect, the method described herein includes diagnosing, identifying or monitoring the onset or recurrence of a disease or condition, such as a cancer, in a subject in need of therapeutic intervention. In one embodiment, the method includes isolating rRNA fragments from a cell, tissue or body fluid obtained from the subject; hybridizing the rRNA fragments to a panel of oligonucleotides engineered to detect rRNA fragments; analyzing an identity and levels of the rRNA fragments present in the cell; wherein a differential in the identity or measured rRNA fragments' levels to the reference is indicative of a diagnosis or identification of breast cancer in the subject; and providing a treatment regimen to the subject dependent on the differential in the identity and measured rRNA fragments' levels to the reference.

The non-coding RNAs of interest (rRNAs or tRNAs) may be isolated by a method known in the art or selected from the group consisting of size selection, amplification and sequencing.

In some embodiments, the size of the rRNA or tRNA fragments is in the range of about 10 nucleotides to about 60 nucleotides are isolated. The range of sizes may include, but are not limited to, from about 15 nucleotides to about 50 nucleotides, and from about 20 nucleotides to about 45 nucleotides. The size of the rRNAs fragments may be about 10 nucleotides, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or about 60 nucleotides.

The signature is an rRNA or tRNA fragment profile that comprises the identity, abundance and relative abundance of rRNA or tRNA fragments. The rRNA or tRNA fragments' location within the genomic loci of origin, the starting and ending points of the fragments, the length of the fragments, and any other feature of the fragments as compared to other rRNA or tRNA fragments within the same sample or another sample or reference may be included in the rRNA or tRNA fragment signature. In one embodiment, the signature is obtained by hybridization to a single oligonucleotide, or to a panel of oligonucleotides, such as those that comprise at least two or more oligonucleotides that selectively hybridize to the rRNA or tRNA fragments. To prepare the sample for characterization, the rRNAs, tRNAs, rRNA fragments or tRNA fragments may be amplified prior to the hybridization.

The therapeutic methods disclosed herein, including prophylactic treatment, to treat a disease or condition, such as a disease selected from the group consisting of a cancer, and genetically predisposed disease in a subject, include administering a therapeutically effective amount of an agent or therapeutic to a subject (e.g., animal, human) in need thereof, including a mammal, particularly a human. Such treatment is suitably administered to subjects, particularly humans, suffering from, having, susceptible to, or at risk for the disease or condition or a symptom thereof. The agent may be identified in a screening assay using signatures of rRNA fragments or relative abundances of rRNA fragments in in vitro or in vivo animal model for the disease or condition.

Monitoring

Methods of monitoring subjects that are at risk of developing a disease or condition, or are at risk of disease or condition recurrence, or who are receiving therapeutic intervention to reduce, improve, or treat a symptom of the disease or condition, such as breast cancer, are also useful in determining whether to administer treatment and in managing treatment. Provided are methods where the rRNA fragments are measured and characterized. In some cases, the rRNA fragments are measured and characterized as part of a routine course of action. In other cases, the rRNA fragments are measured and characterized before and again after subject management or treatment. In these cases, the methods are used to monitor the onset of a disease or condition, the recurrence of the disease or condition, the status of the disease or condition, or a propensity to develop such disease or condition, e.g., cancer, Alzheimer's disease, glaucoma, etc.

For example, characterization of rRNA fragments or signatures can be used to monitor a subject's response to certain treatments. Such characterization can be used to monitor for the presence or absence of the disease or condition. The changes in the relative abundance or rRNA signature delineated herein before treatment, during treatment, or following the conclusion of a treatment regimen may be indicative of the course of the disease or condition, progression of disease or condition, or response to treatment. In some embodiments, characterization of rRNA fragments or signatures may be assessed at one or more times (e.g., 2, 3, 4, 5). Analysis of the rRNA fragments is made, for example, using a size selection, sequencing, and amplification, or other standard method to determine the rRNA fragment profile. If desired, the rRNA fragment profile is compared to a reference to determine if any alteration in the rRNA fragment profile is present. Such monitoring may be useful, for example, in assessing the efficacy of a particular treatment in a patient. Therapeutics that normalize the rRNA fragment profile are taken as particularly useful.

Kits

Kits for diagnosing, identifying or monitoring a disease or condition, such as a cancer or a glaucoma, are included. In one aspect, the invention includes a panel of engineered oligonucleotides comprising a mixture of oligonucleotides that are about 5 to about 15 nucleotides (nts) in length and capable of hybridizing RNAs (e.g. rRNAs or tRNA) and RNA fragments, wherein the RNAs and RNA fragments are less than about 60 nts in length. In another aspect, the invention includes a kit for high-throughput analysis of RNA or RNA fragments in a sample comprising the panel of engineered oligonucleotides of this invention along with hybridization reagents and RNA isolation reagents. In another aspect, the invention includes a kit for high-throughput analysis of RNA or RNA fragments in a sample comprising a set of specially designed TaqMan® assays aimed at measuring the abundance of molecules mentioned in this invention. Alternatively, the kit could include: a specially designed TaqMan® Gene Expression Assays, TaqMan® Low Density Array-micro fluidic cards; a set of end-point specific assays such as dumbbell-PCR; a set of miR-ID assays. Other kits with variations on the components and oligonucleotide panels may be used in the context of the present invention. For example, the panel of engineered oligonucleotides or specially-designed kit may be specific to a cell type, disease type, stage of disease, or other aspect that may differentiate RNA fragment signatures. The kits and oligonucleotide panel may also be used to identify agents that modulate disease, or progression of disease in in vitro or in vivo animal models for the disease. In some embodiments, the subject in need thereof is a human.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Results of the experiments disclosed herein are now described.

The present invention described herein includes by reference several datasets of short RNA profiles. Collections of RNA fragments (rRNA and tRNA) were identified and analyzed for several datasets. The results of the analyses are summarized in 42 tables (Table 10-Table 51) on a compact disc (CD) created on Dec. 22, 2016 that were submitted with the Provisional Patent Application No. 62/498,368 and in tables 52-55. The details of these results are located in the files listed in FIG. 6 and below herein.

| | |
|---|---|
| ALL_rRNA_seqs.1000GenomesProject@atleast10RPM.Population-Sex-Location.27November2016_All | Table 10 |
| ALL_rRNA_seqs.1000GenomesProject@atleast10RPM.Population-Sex-Location.27November2016_more20percent | Table 11 |
| ALL_rRNA_seqs.BrainSamples@atleast1000reads.Location.27November2016 | Table 12 |
| ALL_rRNA_seqs.NormalBcells_and_CLL@atleast1000reads.Location.27November2016 | Table 13 |
| ALL_rRNA_seqs.NormalBcells_and_POAG@atleast10RPM.10December2016 | Table 14 |
| ALL_rRNA_seqs.NormalBcells_and_TNBC@atleast10RPM.Location.27November2016_All | Table 15 |
| ALL_rRNA_seqs.NormalBreast_and_TNBC@atleast10RPM.Location.27November2016_more20percent | Table 16 |
| ALL_rRNA_seqs.PlateletSamples@atleast1000reads.Location.27November2016 | Table 17 |
| ALL_rRNA_seqs.ProstateSamples@atleast1000reads.Location.27November2016 | Table 18 |
| ALL_rRNA_seqs.TCGAProject@atleast10RPM.CancerType-Location.27November2016_All | Table 19 |
| ALL_rRNA_seqs.TCGAProject@atleast10RPM.CancerType-Location.27November2016_more20percent | Table 20 |
| ALL_rRNA_seqs.TCGAProject@atleast10RPM.CancerType-Location.27November2016_more20percentResort | Table 21 |
| ALL_rRNA_seqs.POAG_exclusive.and.NOT_in_LCL.NOT_in_TCGA_NOT_inNormalandCLL.sequences.txt | Table 22 |
| ALL.NormalBcells_and_POAG.exclusive.transfer_RNA_Fragments.10RPMormore.12December2016.txt | Table 23 |
| ALL_tRNA_seqs.exclusive.transfer_RNAs.10RPMormore.POAG_exclusive.and.NOT_in_LCL.NOT_in_TCGA.sequences.txt | Table 24 |
| SAM.1000GenomesProject.CEU_vs_FIN_GBR_TSI@FDR=0.0_NegatSign | Table 25 |
| SAM.1000GenomesProject.CEU_vs_FIN_GBR_TSI@FDR=0.0_PositSign | Table 26 |
| SAM.1000GenomesProject.Men.CEU_YRI@FDR=0.0_NegatSign | Table 27 |
| SAM.1000GenomesProject.Men.CEU_YRI@FDR=0.0_PositSign | Table 28 |
| SAM.1000GenomesProject.Men_Women.CEU@FDR=0.0_NegatSign | Table 29 |
| SAM.1000GenomesProject.Men_Women.CEU@FDR=0.0_PositSign | Table 30 |
| SAM.1000GenomesProject.Men_Women.FIN@FDR=0.0_NegatSign | Table 31 |
| SAM.1000GenomesProject.Men_Women.FIN@FDR=0.0_PositSign | Table 32 |
| SAM.1000GenomesProject.Men_Women.GBR@FDR=0.0_NegatSign | Table 33 |
| SAM.1000GenomesProject.Men_Women.GBR@FDR=0.0_PositSign | Table 34 |
| SAM.1000GenomesProject.Men_Women.TSI@FDR=0.0_NegatSign | Table 35 |
| SAM.1000GenomesProject.Men_Women.TSI@FDR=0.0_PositSign | Table 36 |
| SAM.1000GenomesProject.Men_Women.YRI@FDR=0.0_NegatSign | Table 37 |
| SAM.1000GenomesProject.Men_Women.YRI@FDR=0.0_PositSign | Table 38 |
| SAM.1000GenomesProject.Women.CEU_YRI@FDR=0.0_NegatSign | Table 39 |
| SAM.1000GenomesProject.Women.CEU_YRI@FDR=0.0_PositSign | Table 40 |
| SAM.NormalBcells_and_CLL@FDR=0.0_NegatSign | Table 41 |
| SAM.NormalBcells_and_CLL@FDR=0.0_PositSign | Table 42 |
| SAM.NormalBcells_and_POAG@FDR=0.05_SAM.PositSign.txt | Table 43 |
| SAM.NormalBreast_and_TNBC@FDR=0.0_NegatSign | Table 44 |
| SAM.NormalBreast_and_TNBC@FDR=0.0_PositSign | Table 45 |
| SAM.TCGAProject.BRCA_vs_therest@FDR=0.0_NegatSign | Table 46 |
| SAM.TCGAProject.BRCA_vs_therest@FDR=0.0_PositSign | Table 47 |
| SAM.TCGAProject.PAAD_vs_therest@FDR=0.0_NegatSign | Table 48 |

| | |
|---|---|
| SAM.TCGAProject.PAAD_vs_therest@FDR=0.0_PositSign | Table 49 |
| SAM.TCGAProject.PRAD_vs_therest@FDR=0.0_NegatSign | Table 50 |
| SAM.TCGAProject.PRAD_vs_therest@FDR=0.0_PositSign | Table 51 |

Part of Tables 10, 12-18, 20, 22, 24 and 52-55 is also provided elsewhere herein (after Example 11, at the end of the Examples section).

Example 1: Genomic Arrangement and Sequences of rRNAs

The schematic in FIG. 1 shows the arrangement of the six rRNA sequences used herein within their genomic context.

Example of sequences used in this invention are listed in FIG. 2-FIG. 5. With the exception of the mitochondrial 12S and 16S, the remaining rRNAs (5S, 18S, 5.8S and 28S) have multiple genomic copies that are largely identical. In the sequences listed in FIG. 2-FIG. 5 (SEQ ID NO: 71881-71884), all rRNAs have been padded on both sides with additional sequences to account for sequencing reads that might extend past the natural boundaries of the rRNA. The degree of padding differs in each case. The padded sequences are shown in lower case letters. The actual rRNA sequences, or of the pre-rRNA in the case of 45S, are shown in upper case letters. In the case of 45S pre-RNA, spacer sequences are shown in black upper case letters whereas the actual rRNA sequences are shown in color (grey) upper case letters and underlined; the sequences preceding the 18S rRNA or following the 28S rRNA do not produce rRNA and are also shown in black upper case letters. The color (grey scale) used is the same as the color used in the Tables listed herein (Excel spreadsheets) to indicate the respective rRNA. In the case of 45S the three rRNAs shown in FIG. 5 appear in this order: 18S, 5.8S and 28S; on the other hand, in the Tables (Excel files) provided herein on a CD, which was submitted with the Provisional Patent Application No. 62/498,368, (filed Dec. 22, 2016), the grey scale color is used to highlight the entire 45S pre-RNA sequence, which includes the 18S, 5.8S and 28S rRNAs as well as sequences that do not produce rRNAs.

Example 2: Analysis of rRNAs

Adapter sequences were removed from the sequenced reads and the reads were quality trimmed and mapped on the sequences shown in FIGS. 2-5. Only reads that were at least 16 nts in length and mapped exactly on the studied sequences were considered in the present analysis.

A molecule's abundance was calculated in terms of Reads per Million (RPM) as follows: the number of reads supporting the presence of a specific molecule was normalized by dividing by the total number of sequenced reads that remained after adapter removal and quality trimming then multiplied by 1,000,000. Only molecules whose abundance was at least 10 RPM (stringent) were considered in the present analysis.

Datasets

The following datasets were analyzed 492 datasets from the 1000 Genomes Project (1KG) representing healthy men and women, from five human population groups (CEU, FIN, GBR, TSI, and YRI), and two races (White and Black). The datasets are publicly available and were obtained by sequencing immortalized B-cells (lymphoblastoid cell lines or LCL).

10274 datasets from The Cancer Genome Atlas (TCGA). The datasets are publicly available and were obtained by sequencing primary patient samples that represent 32 cancer types.

18 Triple Negative Breast Cancer (TNBC) samples and 21 normal breast samples from Wh and B/Aa subjects. The datasets were obtained and sequenced as part of ongoing projects. These datasets are not publicly available yet.

10 datasets generated by sequencing 5 B-cell enriched PBMC samples from healthy individuals and 5 PBMC samples from chronic lymphocytic leukemia (CLL) patients. The datasets are publicly available and were obtained and sequenced as part of earlier projects.

4 datasets from human brain. The datasets were generated by sequencing 2 normal brain samples and 2 brain samples from patients with Alzheimer's disease. The datasets are publicly available and were obtained and sequenced as part of earlier projects.

10 datasets generated by sequencing 10 platelet samples from healthy men. The datasets were obtained and sequenced as part of earlier projects. These datasets are not publicly available yet.

10 datasets generated by sequencing 5 normal prostate samples and 5 prostate cancer samples. The datasets are publicly available and were obtained and sequenced as part of earlier projects.

Overall Results

The analysis of the datasets listed above herein demonstrates that all 6 rRNAs give rise to multiple fragments. There is the formal possibility that these fragments might be degradation products. However, in recent years, multiple lines of evidence from investigations of miRNAs and tRNAs showed that the seemingly random products were in fact non-random.

Further investigation of the datasets used herein revealed the following:

all six rRNAs produce fragments of varying lengths;

these rRNA fragments (heretofore referred to as "rRFs") are produced in a constitutive manner and, thus, are not degradation products;

the levels and composition of rRFs depend on a person's sex;

the levels and composition of rRFs depend on a person's population origin;

the levels and composition of rRFs depend on a person's race;

the levels and composition of rRFs depend on tissue;

the levels and composition of rRFs depend on tissue state;

the levels and composition of rRFs depend on disease and disease subtype.

Clearly, the results of rRNAs analysis showed that rRNA fragments are constitutive and not degradation products, and that their levels depend on a person's sex, population, and race as well as on tissue, tissue state, disease, and disease subtype, and possibly other variables.

Example 3: Results from the 1000 Genomes Project 492 datasets from the 1KG project were analyzed. The datasets represent healthy men and women, from five human population groups: CEU (Utah residents of Northern and Western European descent), FIN (Finns), GBR (Brits and Scotts), TSI (Toscani Italians), and YRI (Yoruba Africans from the city of Ibadan). Within a population group, there was an even representation of men and women (~50% of each sex). Four of the population groups were White (see Definitions above)—CEU, FIN, GBR and TSI—and one was Black (YRI).

In the CD submitted with the Provisional Patent Application No. 62/498,368, (filed Dec. 22, 2016), Table 10 (SEQ ID NOs: 6525-28515) (ALL_rRNA_seqs.1000Genomes Project@atleast10RPM.Population-Sex-Location.27November2016) and Table 11 (SEQ ID NOs: 1-6524) (ALL_rRNA_seqs.1000GenomesProject@atleast10RPM.Population-Sex-Location.27November2016_more20percent) summarize the findings. The Excel file shows for each of the analyzed rRNAs the following information:

which rRFs are made from each rRNA sequence
where each rRF is located in the (padded) analyzed sequence
where each rRF is located within the corresponding rRNA sequence
the strand of the rRNA sequence from which each rRF is produced
the length of each rRF
the sequence of each rRF
the portion of the available datasets in which the rRF is present at an abundance of at least 10 RPM: specifically, the last portion for the following groups of datasets is reported herein below: CEU MALE, FIN MALE, GBR MALE, TSI MALE, YRI MALE, CEU FEMALE, FIN FEMALE, GBR FEMALE, TSI FEMALE, and YRI FEMALE.

For example a line that reads as illustrated in Table 1 below, is interpreted as follows:

Table 1.

the fragment is present at an abundance ≥10 RPM in 37.3% of the analyzed datasets from Males from the CEU population group 73.0% of the analyzed datasets from Males from the FIN population group 66.7% of the analyzed datasets from Males from the GBR population group 76.4% of the analyzed datasets from Males from the TSI population group 32.5% of the analyzed datasets from Males from the YRI population group 24.4% of the analyzed datasets from Females from the CEU population group 79.7% of the analyzed datasets from Females from the FIN population group 56.0% of the analyzed datasets from Females from the GBR population group 72.7% of the analyzed datasets from Females from the TSI population group 38.2% of the analyzed datasets from Females from the YRI population group.

Of note is the relative dearth (a ~1:2 ratio) of this fragment in CEU and YRI Males (light grey highlight) compared to FIN and TSI Males (dark grey highlight). An analogous comment can be made for CEU and YRI Females (light grey highlight) compared to FIN and TSI Females (dark grey highlight) as well.

Other Comments and Statistics:

a) Cells in the above mentioned tables have been color-coded (different intensity range in grey scale) to make it easier to visually identify groupings based on rRF lengths, in which population-sex combination is a fragment frequent, etc.

b) Table 11 (labeled "in ≥20% of Pop-Sex-group sets") lists the subset of rRFs that are present in at least 20% of the datasets in at least one of the shown combinations of Population-group+Sex.

c) There are 21991 distinct rRFs that appear with a normalized abundance of ≥10 RPM in at least one of the analyzed datasets (T: 553 arise from the 5S rRNA, 1734 arise from the 12S rRNA, 3055 arise from the 16S rRNA, and 16649 arise from the 45S rRNA.

TABLE 1

| | |
|---|---|
| 37.3% | CEU MALE |
| 73.0% | FIN MALE |
| 66.7% | GBR MALE |
| 76.4% | TSI MALE |
| 32.5% | YRI MALE |
| 24.4% | CEU FEMALE |
| 79.7% | FIN FEMALE |
| 56.0% | GBR FEMALE |
| 72.7% | TSI FEMALE |
| 38.2% | YRI FEMALE |
| Hg38\| 05S_plus 10_biPad | rRNA that was processed and contains the fragment (all rRNA sequences that we processed were padded) |
| + | Strand |
| 3 | From coordinate (local coordinate in actual rRNA) |
| 32 | To coordinate (local coordinate in actual rRNA) |
| 30 | Length fragment |
| CTACGGGCCATACCACCCTGAACGCGCCCGA | Sequences of fragment |
| 13 | From coordinate (local coordinate in padded rRNA) |
| 42 | to coordinate (local coordinate in padded rRNA) | there is a fragment that arises from the 5S rRNA and whose sequence is CTACGGCCATACCACCCTGAACGCGCCCGA (SEQ ID NO: 15)
the fragment's length is 30 nts;
the fragment spans locations 3 through 32 inclusive of the archetype 5S rRNA;

d) There are 6524 distinct rRFs that appear with a normalized abundance of ≥10 RPM in at least 20% of the datasets of a given Population-group+Sex combination: 212 arise from the 5S rRNA, 611 arise from the 12S rRNA, 1043 arise from the 16S rRNA, and 4658 arise from the 45S rRNA.

Individual rRFs are Present/Absent in a Sex-Specific Manner

As an example, the rRF with sequence AGGTGAAAT-TCTTGGAC (SEQ ID NO: 2485), from the 18S rRNA that spans locations 4611 through 4627 inclusive of the 45S pre-rRNA, is noted. This particular rRF is more frequent in females from the CEU Population-group compared to males from the same group at a ratio of nearly 2:1. This skewed representation is absent from the males:females comparisons in the remaining four Population-groups.

As a second example, the rRF with sequence GAAAGTCGGAGGTTCGAAGACGATC (SEQ ID NO: 2627), from the 18S rRNA that spans locations 4687 through 4711 inclusive of the 45S pre-rRNA, is noted. This particular rRF is more frequent in males from the CEU Population-group compared to females from the same group at a ratio of nearly 2.5:1. This skewed representation is also present in the GBR (2:1) and TSI (2:1) Population-groups but absent from the males:females comparisons in the remaining two Population-groups.

As a third example, the rRF with sequence AACTAGTTACGCGACC (SEQ ID NO: 3212), from the 18S rRNA that spans locations 5055 through 5070 inclusive of the 45S pre-rRNA, is noted. This particular rRF is more frequent in females from the CEU Population-group compared to males from the same group at a ratio of nearly 3:1. This skewed representation is absent from the males:females comparisons in the remaining four Population-groups.

Individual rRFs are Present/Absent in a Population-Group-Specific Manner

As an example, the rRF with sequence CCGCCCTACCCCCCCGGCCCCG (SEQ ID NO: 5336), from the 28S rRNA that spans locations 11359 through 11380 inclusive of the 45S pre-rRNA, is noted. This particular rRF is present in at least ½ of all datasets from the CEU Population-group with an abundance of ≥10 RPM whereas it is virtually absent from the remaining Wh (FIN, GBR, TSI) and B/Aa (YRI) Population-groups. This observation is true for both males and females.

Individual rRFs are Present/Absent in a Race-Specific Manner

As an example, the rRF with sequence AAACGCTTAGCCTAGCCACACCC (SEQ ID NO: 233), from the 12S rRNA where it spans locations 135 through 137 inclusive, is noted. This particular rRF is present in at least ⅔rds of all datasets involving one of the four Wh Population-groups (CEU, FIN, GBR, TSI) with an abundance of ≥10 RPM whereas it is virtually absent from the YRI Population-group. This observation is true for both males and females.

As a second example, the rRF with sequence CGGGCCGCCGGTGAAATACCACTAC (SEQ ID NO: 5844), from the 28S rRNA that spans locations 11954 through 11978 inclusive of the 45S pre-rRNA, is noted. This particular rRF is present in virtually all datasets from the B/Aa Population-group (YRI) with an abundance of ≥10 RPM whereas it is present in ~⅓rd or fewer of the datasets from the four Wh Population-groups (CEU, FIN, GBR, TSI). This observation is true for both males and females.

Combination of rRFs are Present/Absent in a Sex-Specific, Population-Group-Specific, or Race-Specific Manner From the above description, it should be understood that it is not only those rRFs that are present or absent from specific groups of individuals are useful. In fact, even if a collection of multiple rRFs is present in all e.g. Population-group+Sex combinations the relative abundance of these rRFs could still change in a manner that changes from each Population-group+Sex combination to the next, and thus can be used to determine a subject's e.g. Population-group+Sex combination. To examine this possibility, all rRFs that were identified in these 492 datasets were analyzed using the Significance Analysis of Microarrays (SAM) method variant that is applicable to RNA-seq datasets. For this analysis, the very strict False Discovery Rate (FDR) threshold of 0.0 was enforced. The following combinations were examined:

Sex-Comparison—Single Population-Group and, Thus, Single Race-Group
- Males vs Females from the CEU Population-group
- Males vs Females from the FIN Population-group
- Males vs Females from the GBR Population-group
- Males vs Females from the TSI Population-group
- Males vs Females from the YRI Population-group Population Group-Comparison—Both Sexes—Single Race-Group
- All CEU datasets (males and females) vs All remaining datasets (males and females) of the same race Race-Comparison—Single Sex-Group
- Males from the CEU Population-group (Wh) vs Males from the YRI Population-group (B/Aa)
- Females from the CEU Population-group (Wh) vs Females from the YRI Population-group (B/Aa)

In all of the above comparisons, specific combinations of rRFs were found that could clearly distinguish between the datasets that were being compared each time. Combinations of rRFs were found that were more abundant
- in females from a given Population-group;
- in males from a given Population-group;
- in a given Population-group vs. other Population-groups of the same Race-group;
- in males from a given Race-group; or,
- in females from a given Race-group.

In summary, it was found that these signatures comprised various combinations of 15072 unique rRFs: of these, 10832 appear only in one signature, i.e. they are relevant for exactly one of the above comparisons—this suggests an exquisite degree of context-specific expression. Clearly, many more unique rRFs are expected to be identified if signatures are sought for other combinations of datasets. Table 2 below lists the numbers of distinct rRFs that emerge from each comparison and the filenames of the files included in the CD submitted with the Provisional Patent Application No. 62/498,368, filed Dec. 22, 2016. Files whose filename ends in "NegatSign.txt" list rRFs whose abundance decreases in the second of the two groups being compared. Files whose filename ends in "PositSign.txt" list rRFs whose abundance increases in the second of the two groups being compared.

Table 2.

TABLE 2

| Number of rRFs in signature | Filename | Comparison |
|---|---|---|
| 38 | SAM.1000GenomesProject.Men_Women.CEU@FDR=0.0_PositSign.txt | Males vs Females-CEU Population-group (Table 30) |
| 60 | SAM.1000GenomesProject.Men_Women.FIN@FDR=0.0_PositSign.txt | Males vs Females-FIN Population-group (Table 32) |

TABLE 2-continued

| Number of rRFs in signature | Filename | Comparison |
|---|---|---|
| 29 | SAM.1000GenomesProject.Men_Women.GBR@FDR=0.0_PositSign.txt | Males vs Females-GBR Population-group (Table 34) |
| 11576 | SAM.1000GenomesProject.Men_Women.TSI@FDR=0.0_NegatSign.txt | Males vs Females-TSI Population-group (Table 35) |
| 46 | SAM.1000GenomesProject.Men_Women.YRI@FDR=0.0_PositSign.txt | Males vs Females-YRI Population-group (Table 38) |
| 1202 | SAM.1000GenomesProject.CEU_vs_FIN_GBR_TSI@FDR=0.0_NegatSign.txt | CEU (males and females) vs the remaining three Population-groups of the same race (FIN, GBR, TSI) (Table 25) |
| 144 | SAM.1000GenomesProject.CEU_vs_FIN_GBR_TSI@FDR=0.0_PositSign.txt | CEU (males and females) vs the remaining three Population-groups of the same race (FIN, GBR, TSI) (Table 26) |
| 2939 | SAM.1000GenomesProject.Men.CEU_YRI@FDR=0.0_NegatSign.txt | Males from the CEU Population-group (White) vs Males from the YRI Population-group (Black) (Table 27) |
| 3 | SAM.1000GenomesProject.Men.CEU_YRI@FDR=0.0_PositSign.txt | Males from the CEU Population-group (White) vs Males from the YRI Population-group (Black) (Table 28) |
| 4710 | SAM.1000GenomesProject.Women.CEU_YRI@FDR=0.0_NegatSign.txt | Females from the CEU Population-group (White) vs Females from the YRI Population-group (Black) (Table 39) |
| 34 | SAM.1000GenomesProject.Women.CEU_YRI@FDR=0.0_PositSign.txt | Females from the CEU Population-group (White) vs Females from the YRI Population-group (Black) (Table 40) |

Example 4: Results from the Cancer Genome Atlas TCGA 10274 datasets from the TCGA project were analyzed. The datasets represent 32 cancer types. The 32 cancers that were analyzed, together with their abbreviations, are listed below herein:

ACC-Adrenocortical carcinoma, BLCA-Bladder Urothelial Carcinoma, BRCA-Breast invasive carcinoma, CESC-Cervical squamous cell carcinoma and endocervical adenocarcinoma, CHOL-Cholangiocarcinoma, COAD-Colon adenocarcinoma, DLBC-Lymphoid Neoplasm Diffuse Large B-cell Lymphoma, ESCA-Esophageal carcinoma, HNSC-Head and Neck squamous cell carcinoma, KICH-Kidney Chromophobe, KIRC-Kidney renal clear cell carcinoma, KIRP-Kidney renal papillary cell carcinoma, LAML-Acute Myeloid Leukemia, LGG-Brain Lower Grade Glioma, LIHC-Liver hepatocellular carcinoma, LUAD-Lung adenocarcinoma, LUSC-Lung squamous cell carcinoma, MESO-Mesothelioma, OV-Ovarian serous cystadenocarcinoma, PAAD-Pancreatic adenocarcinoma, PCPG-Pheochromocytoma and Paraganglioma, PRAD-Prostate adenocarcinoma, READ-Rectum adenocarcinoma, SARC-Sarcoma, SKCM-Skin Cutaneous Melanoma, STAD-Stomach adenocarcinoma, TGCT-Testicular Germ Cell Tumors, THCA-Thyroid carcinoma, THYM-Thymoma, UCEC-Uterine Corpus Endometrial Carcinoma, UCS-Uterine Carcinosarcoma, and UVM-Uveal Melanoma. In all, 79 ACC, 386 BLCA, 1176 BRCA, 304 CESC, 44 CHOL, 395 COAD, 46 DLBC, 196 ESCA, 528 HNSC, 83 KICH, 519 KIRC, 291 KIRP, 191 LAML, 514 LGG, 403 LIHC, 480 LUAD, 461 LUSC, 82 MESO, 461 OV, 157 PAAD, 186 PCPG, 527 PRAD, 146 READ, 248 SARC, 410 SKCM, 479 STAD, 138 TGCT, 547 THCA, 124 THYM, 536 UCEC, 57 UCS, and 80 UVM datasets were analyzed.

In the CD submitted with the Provisional Patent Application No. 62/498,368, (filed Dec. 22, 2016) Table 19 (ALL_rRNA_seqs.TCGAProject@atleast10 RPM.CancerType-Location.27November2016), Table 20 (ALL_rRNA_seqs.TCGAProject@atleast10RPM.CancerType-Location.27November2016 more20percent) and Table 21 (ALL_rRNA_seqs.TCGAProject@atleast10RPM.CancerType-Location.27November2016_more20percentResort) summarize the findings. These tables show for each of the analyzed rRNAs (SEQ ID NOs: 28516-56828) the following information:

which rRFs are made from each rRNA sequence
where each rRF is located in the (padded) analyzed sequence
where each rRF is located within the corresponding rRNA sequence
the strand of the rRNA sequence from which each rRF is produced
the length of each rRF
the sequence of each rRF
the portion of the available datasets from each cancer type (out of the 32 cancer types mentioned above herein) in which the rRF is present at an abundance of at least 10 RPM: specifically. The 32 cancer types are listed in alphabetical order using their above-mentioned abbreviation.

For example a line that reads as illustrated in Table 3 below, is interpreted as follows:

Table 3.

TABLE 3

| | |
|---|---|
| 2.5% | ACC |
| 2.1% | BLCA |

TABLE 3-continued

| | |
|---|---|
| 0.9% | BRCA |
| 2.6% | CESC |
| | CHOL |
| 2.8% | COAD |
| 2.2% | DLBC |
| 1.0% | ESCA |
| 2.5% | HNSC |
| | KICH |
| 2.3% | KIRC |
| | KIRP |
| 1.6% | LAML |
| 0.2% | LGG |
| 1.0% | LIHC |
| 0.6% | LUAD |
| 7.6% | LUSC |
| | MESO |
| 79.0% | OV |
| | PAAD |
| | PCPG |
| 0.2% | PRAD |
| 2.1% | READ |
| 0.4% | SARC |
| 2.7% | SKCM |
| 1.0% | STAD |
| 1.4% | TGCT |
| | THCA |
| | THYM |
| 2.2% | UCEC |
| 5.3% | UCS |
| | UVM |
| Hg38\| 458_plus 10000_biPad | rRNA that was processed and contains the fragment (all rRNA sequences that we processed were padded) |
| + | Strand |
| 10815 | from coordinate (local coordinate in actual rRNA) |
| 10837 | to coordinate (local coordinate in actual rRNA) |
| 23 | length of fragment |
| TCTAAGGGCTGGGTCGGTCGGGC | Sequences of fragment |
| 20815 | from coordinate (local coordinate in padded rRNA) |
| 20837 | to coordinate (local coordinate in padded rRNA) | there is a fragment that arises from the 28S rRNA (45S pre-rRNA) and whose sequence is TCTAAGGGCTGGGTCGGTCGGGC (SEQ ID NO: 30186)

the fragment's length is 23 nts;

the fragment spans locations 10815 through 10837 inclusive of the 45S pre-rRNA sequence;

the fragment is present at an abundance ≥10 RPM in 79% (364 out of 461) of the OV-Ovarian serous cystadenocarcinoma samples analyzed (illustrated by a dark color of the cell);

the fragment is absent from virtually all other cancer types as indicated by the shown percentages (illustrated by a light/white color of the cell).

Other Results and Statistics:

a) Cells in the above-mentioned table have been color-coded (different intensity range in grey scale) to make it easier to visually identify groupings based on rRF lengths, in which cancer type is a fragment frequent etc.

b) Table 20 (in the Provisional Patent Application No. 62/498,368; labeled "in ≥20% of Cancer sets") lists the subset of rRFs that are present in at least 20% of the datasets in at least one of the 32 cancer types. The above OV-specific rRF is a characteristic such example.

c) Table 21 (in the Provisional Patent Application No. 62/498,368; labeled "in ≥20% of Cancer sets-Resorted") lists the same collection of rRFs as Table 20 but sorted in an order that highlights rRFs that are specific for various combinations of cancer types.

d) There are 25712 distinct rRFs that appear with a normalized abundance of ≥10 RPM in at least one of the analyzed datasets (SEQ ID NOs: 31117-56828; Table 19 in the Provisional Patent Application No. 62/498,368): 741 arise from the 5S rRNA, 553 arise from the 12S rRNA, 1115 arise from the 16S rRNA, and 23303 arise from the 45S rRNA.

e) There are 2601 distinct rRFs that appear with a normalized abundance of ≥10 RPM in at least 20% of the datasets of a given cancer type (one of 32) (SEQ ID NOs: 28516-31116; Table 20, in the Provisional Patent Application No. 62/498,368): 203 arise from the 5S rRNA, 4 arise from the 12S rRNA, 24 arise from the 16S rRNA, and 2370 arise from the 45S rRNA.

Individual rRFs are Present/Absent in a Cancer-Type-Specific Manner

As an example, the rRF with sequence GGCGCTCTCGCAGACCCGACGC (SEQ ID NO: 29799), from the 28S rRNA that spans locations 9612 through 9633 inclusive of the 45S pre-rRNA, is noted. This particular rRF is present at an abundance ≥10 RPM in 73.3% (140 out of 191) of the LAML-Acute Myeloid Leukemia samples analyzed yet absent from virtually all other TCGA cancer samples.

As a second example, the rRF with sequence CTTCGT-GATCGATGTGGTGACGT (SEQ ID NO: 28751), which spans locations 425 through 447 inclusive of the 45S pre-rRNA, is noted. This particular rRF is present at an abundance ≥10 RPM in 90.6% (125 out of 138) of the TGCT-Testicular Germ Cell Tumors samples analyzed yet absent from nearly all other TCGA cancer samples. NOTE: this last rRF deserves special mention because it arises from a portion of the 45S pre-RNA sequence that does not encode an rRNA. This suggests that in specific settings even regions of 45S pre-RNA that do not encode for one of 18S, 5.8S, or 28S could be differentially abundant.

As a third example, the rRF with sequence CGCTAAAC-CATTCGTAGACGACCTGCTTC (SEQ ID NO: 31054), from the 28S rRNA that spans locations 12282 through 12910 inclusive of the 45S pre-rRNA, is noted. This particular rRF is present at an abundance ≥10 RPM in 79.0% (364 out of 461) the OV-Ovarian serous cystadenocarcinoma samples analyzed, 48.4% (60 out of 124) of the THYM-Thymoma samples analyzed, 42.2% (173 out of 410) of the SKCM-Skin Cutaneous Melanoma samples analyzed, and in 98.8% (79 out of 80) of the UVM-Uveal Melanoma samples analyzed. The rRF is absent from most of the other TCGA cancer samples.

Combinations of rRFs are Present/Absent in a Cancer-Type-Specific Manner

From the above description, it should not be understood that only those rRFs that are present or absent from specific groups of cancer types are useful. In fact, even if a collection of multiple rRFs is present in all 32 cancer types the relative abundance of these rRFs could still change in a manner that changes from each cancer type to the next. One characteristic example is the group of 15 rRFs that arise from the 5' end of the 28S rRNA and (positions 7925 to 7954). These 15 rRFs are present at an abundance of ≥10 RPM in nearly every single one of the 10274 TCGA samples analyzed herein, and, as a result, these rRFs may carry no information. This idea is supported by the findings of specific examples of Cancer-type-specific signatures: rRFs from this specific region as well as rRFs from the remaining five rRNAs participate in the formation of Cancer-type-specific signatures.

To support this statement, all rRFs that were identified in these 10274 datasets were analyzed using the SAM method variant that is applicable to RNA-seq datasets (see above). For this analysis, the very strict FDR threshold of 0.0 was enforced.

The following combinations were examined:

Cancer-Type-Specific
- all samples from BRCA-Breast Invasive Carcinoma vs all other cancer types
- all samples from PAAD-Pancreatic adenocarcinoma vs all other cancer types
- all samples from PRAD-Prostate adenocarcinoma vs all other cancer types In all of the above comparisons, specific combinations of rRFs were found that could clearly distinguish between the datasets that were being compared each time. As already stated, the resulting signatures included rRFs that are present at an abundance of ≥10 RPM in most of the 10274 datasets.

In all, it was found that these signatures comprised various combinations of 2254 unique rRFs: of these, 1506 appear only in one signature, i.e. they are relevant for exactly one of the above Cancer-type comparisons—this suggests an exquisite degree of context-specific expression. Clearly, many more unique rRFs are expected to be identified if signatures are sought for other combinations of datasets. The below Table 4 lists the numbers of distinct rRFs that emerge from each comparison and the filename of the file that is attached. Files whose filename ends in "NegatSign.txt" list rRFs whose abundance decreases in the second of the two groups being compared. Files whose filename ends in "PositSign.txt" list rRFs whose abundance increases in the second of the two groups being compared (These files were included in the CD submitted with the Provisional Patent Application No. 62/498,368, filed Dec. 22, 2016).

Table 4.

TABLE 4

| Number of rRFs in signature | Filename | Comparison |
| --- | --- | --- |
| 371 | SAM.TCGAProject.BRCA_vs_therest@FDR=0.0_NegatSign.txt | Breast cancer datasets vs Datasets from all remaining cancer types (Table 46) |
| 932 | SAM.TCGAProject.BRCA_vs_therest@FDR=0.0_PositSign.txt | Breast cancer datasets vs Datasets from all remaining cancer types (Table 47) |
| 64 | SAM.TCGAProject.PAAD_vs_therest@FDR=0.0_NegatSign.txt | Pancreatic cancer datasets vs Datasets from all remaining cancer types (Table 48) |
| 202 | SAM.TCGAProject.PAAD_vs_therest@FDR=0.0_PositSign.txt | Pancreatic cancer datasets vs Datasets from all remaining cancer types (Table 49) |
| 1183 | SAM.TCGAProject.PRAD_vs_therest@FDR=0.0_NegatSign.txt | Prostate cancer datasets vs Datasets from all remaining cancer types (Table 50) |
| 328 | SAM.TCGAProject.PRAD_vs_therest@FDR=0.0_PositSign.txt | Prostate cancer datasets vs Datasets from all remaining cancer types (Table 51) |

Example 5: Triple Negative Breast Cancer 21 normal breast and 18 TNBC samples that were obtained independently as part of ongoing projects were analyzed. One of the normal samples was sequenced twice and, thus, there are 22 normal datasets. In all, 40 datasets were analyzed.

In the CD submitted with the Provisional Patent Application No. 62/498,368, (filed Dec. 22, 2016), Table 15 (SEQ ID NOs: 58257-61447) (ALL_rRNA_seqs.NormalBreast_and_TNBC@atleast10RPM.Location.27November-2016_All) and Table 16 (SEQ ID NOs: 56829-58256) (ALL_rRNA_seqs.NormalBreast_and_TNBC@atleast10RPM.Location.27November2016_more20percent) summarize the findings. For each of the analyzed rRNAs the following information is listed:

- which rRFs are made from each rRNA sequence
- where each rRF is located in the (padded) analyzed sequence
- where each rRF is located within the corresponding rRNA sequence
- the strand of the rRNA sequence from which each rRF is produced
- the length of each rRF
- the sequence of each rRF
- the portion of the available datasets from each cancer type in which the rRF is present at an abundance of at least 10 RPM: specifically, this question was addressed for each of the 32 cancer types mentioned above. The 32 cancer types are listed in alphabetical order using their above-mentioned abbreviation.

For example a line that reads as illustrated in Table 5 below, is interpreted as follows:
Table 5.

TABLE 5

| | | |
|---|---|---|
| 54.5% | portion of analyzed datasets (22 normal and 18 TNBC) that contain the respective fragment | Normal Breast |
| 22.2% | | Triple Negative Breast Cancer (TNBC) |
| Hg38\| 05S_plus 10_biPad | | rRNA that was processed and contains the fragment(all rRNA sequences that we processed were padded) |
| + | | Strand |
| 1 | | From coordinate (local coordinate in actual rRNA) |
| 24 | | To coordinate (local coordinate in actual rRNA) |
| 24 | | Length of fragment |
| GTCTACGGCCATACCACCCT-GAAC | | sequences of fragment |
| 11 | | from coordinate (local coordinate in padded rRNA) |
| 34 | | To coordinate (local coordinate in padded rRNA) | there is a fragment that arises from the 5S rRNA and whose sequence is GTGTACGGCCATACCACCCT-GAAC (SEQ ID NO: 56829);
the fragment's length is 24 nts;
the fragment spans locations 1 through 24 inclusive of the 5S pre-rRNA sequence that was analyzed;
the fragment is present at an abundance ≥10 RPM in 54.5% (12 out of 22) of the normal breast datasets;
the fragment is present at an abundance ≥10 RPM in 22.2% (4 out of 18) of the TNBC datasets.

Other Results and Statistics:
a) Cells in the above-mentioned table have been color-coded to make it easier to visually identify groupings based on rRF lengths, in which tissue-state (normal vs TNBC) is a fragment frequent etc.
b) Table 16 (labeled "in ≥20% of Tissue-state sets") lists the subset of rRFs that are present in at least 20% of either the normal or of the TNBC datasets.
c) There are 3191 distinct rRFs (Table 15) that appear with a normalized abundance of ≥10 RPM in at least one of the analyzed datasets: 164 arise from the 5S rRNA, 13 arise from the 12S rRNA, 49 arise from the 16S rRNA, and 2965 arise from the 45S rRNA.
d) There are 1428 distinct rRFs that appear with a normalized abundance of ≥10 RPM in at least 20% of the datasets of a tissue-state (normal or TNBC): 119 arise from the 5S rRNA, 4 arise from the 12S rRNA, 22 arise from the 16S rRNA, and 1283 arise from the 45S rRNA.

Combinations of rRFs are Present/Absent in a Tissue-State-Specific Manner

Similarly to what was done with the previous collections, all rRFs that were identified in these 40 datasets were analyzed using the SAM method variant that is applicable to RNA-seq datasets (see above). For this analysis, the very strict FDR threshold of 0.0 was enforced. Only the Normal breast vs TNBC combination was examined and revealed rRF signatures that were characteristic of tissue state and comprised various combinations of 75 unique rRFs. The below Table 6 lists the numbers of distinct rRFs that emerge from this comparison and the filename of the file that is attached. Files whose filename ends in "NegatSign.txt" list rRFs whose abundance decreases in the second of the two groups being compared. Files whose filename ends in "PositSign.txt" list rRFs whose abundance increases in the second of the two groups being compared (These files were included in the CD submitted with the Provisional Patent Application No. 62/498,368, filed Dec. 22, 2016).
Table 6.

TABLE 6

| # of rRFs in signature | Filename | Comparison |
|---|---|---|
| 10 | SAM.NormalBreast_and_TNBC@FDR=0.0_NegatSign.txt | Normal Breast datasets vs TNBC datasets (Table 44) |
| 65 | SAM.NormalBreast_and_TNBC@FDR=0.0_PositSign.txt | Normal Breast datasets vs TNBC datasets (Table 45) |

Example 6: Chronic Lymphocytic Leukemia (CLL)

5 normal B-cell-enriched samples and 5 samples from patients with CLL were analyzed. These samples were obtained independently as part of ongoing projects and were sequenced herein.

Only rRFs that were supported by 1000 or more reads in at least one of the analyzed datasets were kept. In the CD submitted with the Provisional Patent Application No. 62/498,368, (filed Dec. 22, 2016) Table 13 (ALL_rRNA_seqs.NormalBcellsandCLLSamples@atleast1000reads.Location. 27November2016) summarizes the findings. For each of the analyzed rRNAs the following information is listed:
- which rRFs are made from each rRNA sequence
- where each rRF is located in the (padded) analyzed sequence
- where each rRF is located within the corresponding rRNA sequence
- the strand of the rRNA sequence from which each rRF is produced
- the length of each rRF
- the sequence of each rRF The semantics and color coding are the same as in the previous tables.

Other Comments and Statistics:

There are 1270 distinct rRFs that appear with an abundance of ≥1000 reads in at least one of the analyzed datasets: 25 arise from the 5S rRNA, 11 arise from the 12S rRNA, 53 arise from the 16S rRNA, and 1181 arise from the 45S rRNA.

Combinations of rRFs are Present/Absent in a Tissue-State-Specific Manner

Similarly to what was done with the previous collections, all rRFs that were identified in these 10 datasets were analyzed using the SAM method variant that is applicable to RNA-seq datasets (see above). For this analysis, the very strict FDR threshold of 0.0 was enforced. Only the Normal B-cells vs CLL combination was examined and revealed rRF signatures that were characteristic of tissue state and comprised various combinations of 68 unique rRFs. The below Table 7 lists the numbers of distinct rRFs that emerge from this comparison and the filename of the file that is attached.

Files whose filename ends in "NegatSign.txt" list rRFs whose abundance decreases in the second of the two groups being compared. Files whose filename ends in "PositSign.txt" list rRFs whose abundance increases in the second of the two groups being compared (These files were included in the CD submitted with the Provisional Patent Application No. 62/498,368, filed Dec. 22, 2016).
Table 7.

TABLE 7

| # of rRFs in signature | Filename | Comparison |
|---|---|---|
| 65 | SAM.NormalBcells_and_CLL@FDR=0.0_NegatSign.txt | Normal B-cell datasets vs CLL datasets (Table 41) |
| 3 | SAM.NormalBcells_and_CLL@FDR=0.0_PositSign.txt | Normal B-cell datasets vs CLL datasets (Table 42) |

Example 7: Brain 2 normal brain samples and 2 samples from patients with Alzheimer's were analyzed. These samples were obtained independently as part of ongoing projects and were sequenced herein.

Only rRFs that were supported by 1000 or more reads in at least one of the analyzed datasets were kept. In the CD submitted with the Provisional Patent Application No. 62/498,368, (filed Dec. 22, 2016) Table 12 (SEQ ID NOs: 62718-63036) (ALL_rRNA_seqs.BrainSamples@atleast-1000reads.Location.27November2016) summarizes the findings. For each of the analyzed rRNAs the following information is listed:
- which rRFs are made from each rRNA sequence;
- where each rRF is located in the (padded) analyzed sequence;
- where each rRF is located within the corresponding rRNA sequence;
- the strand of the rRNA sequence from which each rRF is produced;
- the length of each rRF;
- the sequence of each rRF The semantics and color coding are the same as in the previous tables.

Other Comments and Statistics:

There are 319 distinct rRFs (Table 12) that appear with an abundance of ≥1000 reads in at least one of the analyzed datasets: 4 arise from the 5S rRNA, 12 arise from the 12S rRNA, 27 arise from the 16S rRNA, and 276 arise from the 45S rRNA.

Example 8: Platelets 10 platelet samples from healthy individuals, all of them males, were analyzed. These samples were obtained independently as part of ongoing projects and were sequenced herein.

Only rRFs that were supported by 1000 or more reads in at least one of the analyzed datasets were kept. In the CD submitted with the Provisional Patent Application No. 62/498,368, (filed Dec. 22, 2016) Table 17 (SEQ ID NOs: 63037-63115) (ALL_rRNA_seqs.PlateletSamples@atleast-1000reads.Location) summarizes the findings. For each of the analyzed rRNAs the following information is listed:
- which rRFs are made from each rRNA sequence
- where each rRF is located in the (padded) analyzed sequence
- where each rRF is located within the corresponding rRNA sequence
- the strand of the rRNA sequence from which each rRF is produced
- the length of each rRF
- the sequence of each rRF The semantics and color coding are the same as in the previous tables.

Other Comments and Statistics:

There are 79 distinct rRFs that appear with an abundance of ≥1000 reads in at least one of the analyzed datasets: 3 arise from the 5S rRNA, 1 arise from the 12S rRNA, 30 arise from the 16S rRNA, and 45 arise from the 45S rRNA.

Example 9: Prostate 5 normal prostate and 5 prostate cancer samples were analyzed. These samples were obtained independently as part of ongoing projects and were sequenced herein.

Only rRFs that were supported by 1000 or more reads in at least one of the analyzed datasets were kept. In the CD submitted with the Provisional Patent Application No. 62/498,368, (filed Dec. 22, 2016) Table 18 (ALL_rRNA_seqs.ProstateSamplesgatleast1000reads.Location) summarizes the findings. For each of the analyzed rRNAs the following information is listed:
- which rRFs are made from each rRNA sequence
- where each rRF is located in the (padded) analyzed sequence
- where each rRF is located within the corresponding rRNA sequence
- the strand of the rRNA sequence from which each rRF is produced
- the length of each rRF
- the sequence of each rRF The semantics and color coding are the same as in the previous tables.

Other Comments and Statistics:

There are 499 distinct rRFs that appear with an abundance of ≥1000 reads in at least one of the analyzed datasets: 3 arise from the 5S rRNA, 13 arise from the 12S rRNA, 32 arise from the 16S rRNA, and 451 arise from the 45S rRNA.

Example 10: Primary Open Angle Glaucoma Datasets in rRNA

The following collection was also analyzed
six datasets generated from the deep sequencing of RNA from B-cells of six individuals. The composition of the group had as follows:
a) two B/Aa women with primary open angle glaucoma (POAG)
b) two Wh women with POAG
c) one healthy B/Aa woman (used as control)
d) one healthy Wh woman (used as control)

Combinations of rRFs are Present/Absent in a Tissue-State-Specific Manner

The analysis of the above datasets made evident that all 6 rRNAs give rise to multiple fragments. In the CD submitted with the Provisional Patent Application No. 62/498,368, (filed Dec. 22, 2016) Table 14 (SEQ ID NOs: 63615-65473) ALL_rRNA_seqs.NormalBcells_and_POAG@atleast10-RPM.10December2016 summarizes some of the findings. The table shows for each of the analyzed rRNAs the following information:
- which rRFs are made from each rRNA sequence
- where each rRF is located in the (padded) analyzed sequence
- where each rRF is located within the corresponding rRNA sequence
- the strand of the rRNA sequence from which each rRF is produced
- the length of each rRF
- the sequence of each rRF
- how many of the datasets in which the rRF is present at an abundance of at least 10 RPM: specifically, this question was addressed for the following groups of datasets: B/Aa Open Angle Glaucoma Patients (Female), B/Aa Control (Female) Wh Open Angle Glaucoma Patients (Female), Wh Control (Female), where "B/Aa" is an abbreviation for "Black/African American" and "Wh" for "White."

For example a line that reads as illustrated in Table 8 below, is interpreted as follows:

Table 8.

TABLE 8

| B/Aa Open Angle Glaucoma Patients (Female) | B/Aa Control (Female) | Wh Open Angle Glaucoma Patients (Female) | Wh Control (Female) | rRNA that was processed and contains the fragment (all rRNA sequences that we processed were padded) | | strand |
|---|---|---|---|---|---|---|
| 2 | 0 | 2 | 0 | hg38\| 16S _plus10_BiPaddings | | + |
| from coor- dinate (local coor- dinate in actual rRNA) | to coor- dinate (local coor- dinate in actual rRNA) | length of frag- ment | | sequence of fragment | from coor- dinate (local coor- dinate in padded rRNA) | to coor- dinate (local coor- dinate in padded rRNA) |
| 496 | 520 | 25 | | CATAGTAGGCCTAAAAGCAGCCACC | 506 | 530 | there is a fragment that arises from the 16S rRNA and whose sequence is CATAGTAGGCCTAAAAGCA-GCCACC (SEQ ID NO: 64360)

the fragment's length is 25 nts the fragment spans locations 496 through 520 inclusive of the archetype 16S rRNA the fragment is present at an abundance ≥10 RPM in all four patients but in none of the controls.

Other Results and Statistics:

a) In the above-mentioned Excel file cells have been color-coded to make it easier to visually identify groupings based on rRF lengths, in which combination of samples is a fragment present, etc.

b) There are 1859 distinct rRFs (Table 14) that appear with a normalized abundance of ≥10 RPM in at least one of the analyzed datasets: 14 arise from the 5S rRNA, 545 arise from the 12S rRNA, 793 arise from the 16S rRNA, and 507 arise from the 45S rRNA.

c) There are 1205 rRFs (Table 22) that appear with a normalized abundance of ≥10 RPM exclusively in POAG samples but are not present in the control samples: 1028 of these 1205, or 85.3%, arise from mitochondrial rRNAs. This is particularly notable considering that mitochondrial processes have been linked to POAG.

Combinations of rRFs are Present/Absent in a Condition-Specific Manner a) When the 1205 rRFs that are exclusive to the POAG samples were compared with the 21,961 rRFs that appear with the same level of abundance (i.e., 10 RPM) in the 492 datasets generated from the B-cells of healthy individuals from the 1000 Genomes Project collection (see above herein) only 459 were found in common. This strongly indicates that the same type of cell (in this case a B-cell) produces rRFs in the POAG state that would not be produced by this cell in the "normal" state.

b) When the 1205 rRFs that are exclusive to the POAG samples were compared with the 590 rRFs that appear with the same level of abundance (i.e., 10 RPM) in the 5 datasets generated from the blood of the CLL patient collection (see above herein) only 76 were found in common. This strongly indicates, again, that the same type of cell (in this case a B-cell) produces rRFs in the POAG disease state that would not be produced by this cell in the CLL disease state.

c) When the 1205 rRFs that are exclusive to the POAG samples were compared with the 41085 rRFs that appear with the same level of abundance (i.e., 10 RPM)

in one or more of the 10274 datasets from TCGA (see above herein)

in one or more of the 492 datasets from the 1000 Genomes Project (see above herein)

in either the 5 control datasets or the 5 CLL datasets (see above herein)

It was found that 676 of these rRFs are unique to the POAG samples. This strongly indicates that these rRFs are likely unique to the POAG disease state as they do not seem to be produced by other cell types, normal and diseased. Of these 676 rRFs, 338 are present exclusively in the B/Aa POAG patients, 121 are present exclusively in the Wh POAG patients, and 217 are present in both the B/Aa and Wh POAG patients. This strongly indicates that there are many more rRFs that are dysregulated solely in the B/Aa POAG patients and are absent in the Wh POAG patients, which is in strong agreement with the fact that glaucoma is five times more frequent in B/Aa compared to Wh, and strikes earlier and progresses faster in B/Aa than in Wh. Additionally, of these 676 rRFs, 629 or 93.0% arise from mitochondrial rRNAs, a particularly notable result considering that mitochondrial processes have been linked to POAG. Table 22 (ALL_rRNA_seqs.POAG_exclusive.and.NOT_in_LCL.NOT_in_TCGA_NOT_in NormalandCLL.sequences.txt, provided in the CD submitted with the Provisional Patent Application No. 62/498,368, filed Dec. 22, 2016) lists these 676 sequences (SEQ ID NO: 65474-66149). These sequences are compelling candidates to serve as blood biomarkers for POAG.

d) From the above description, it should not be understood that only those rRFs that are present with a normalized abundance of ≥10 RPM in at least one of the analyzed datasets are useful. To examine this possibility, we identified all rRFs that arose from with a normalized abundance of ≥3 RPM (Of note: this is a lower threshold than 10 RPM) then analyzed them using the SAM method variant that is applicable to RNA-seq datasets (see also above). Specifically, the 2 control samples were compared against the 4 POAG samples. For this analysis, the very strict FDR threshold of 0.05 was enforced. Table 9 below lists the number of distinct rRFs that emerged from this comparison and the filename of the file that is attached. As mentioned above, files whose filename ends in "PositSign.txt" list rRFs whose abundance increases in the second of the two groups being compared.

Table 9.

TABLE 9

| Number of rRFs in signature | Filename | Comparison |
| --- | --- | --- |
| 271 | SAM.Normal_POAG@FDR=0.05_PositSign.txt (Table 46) | Female Controls vs Female Patients with POAG |

Some rRNA Fragments are Differentially Expressed Between Glaucoma Patients and Controls Additional Datasets 43 lymphoblastoid cell lines were obtained. These were generated from the peripheral B lymphocytes of 43 donors after transformation by the Epstein-Barr virus. Of the 43 donors, 10 were B/Aa and affected by primary open angle glaucoma (POAG)—referred to as group A1

11 were Wh and affected by POAG—referred to as group A2

11 were B/Aa and apparently healthy (served as controls)—referred to as group B1

11 were Wh and apparently healthy (served as controls)—referred to as group B2

Notably, all 43 donors were female and were selected on purpose.

All 43 datasets were deep sequenced. Subsequently, the rRFs that arose from each of the 6 rRNAs (i.e. 5S, 12S, 16S, 18S, 5.8S, and 28S) were enumerated and their support in terms of sequenced reads was determined.

Findings

DESeq (Love, Huber and Anders Genome Biology 2014) was used and the following comparisons were carried out: A1 vs B1 (i.e. POAG vs. control in B/Aa individuals, see Table 53) and A2 vs B2 (i.e. POAG vs. control in Wh individuals, see Table 53). We sub-selected only those rRFs whose abundance ranked them in the top 60%, had a fold change ≥2× and an FDR ≤0.05.

139 rRFS were found to be differentially expressed between A2 and B2 (i.e. POAG vs. control in Wh individuals). These sequences are listed in Table 52 (SEQ ID NOs: 70852-71219).

368 rRFs were found to be differentially expressed between A1 and B1 (i.e. POAG vs. control in B/Aa individuals). These sequences are listed in Table 53. (SEQ ID NOs: 71220-71358).

Only 23 of these rRFs were differentially expressed between POAG and controls, in both the Wh and B/Aa individuals.

Example 11: Primary Open Angle Glaucoma Datasets in tRNA

Combinations of tRFs are Present/Absent in a Condition-Specific Manner

In previous work, tRNAs encoded in both the nucleus and the mitochondria was reported to give rise to multiple tRFs that are constitutive and not degradation products. Also the levels of tRFs was shown to depend on a person's sex, population, and race as well as on tissue, tissue state, disease, and disease subtype. tRFs possibly depend on other variables too.

Results
1) In the CD submitted with the Provisional Patent Application No. 62/498,368, (filed Dec. 22, 2016) Table 23 (A tab-separated, plaintext file ALL.Normal-Bcells_and_POAG.exclusive.transfer_RNA_fragments.10RPMormore.12December2016.txt) summarizes our findings from the analysis of the above six datasets (SEQ ID NO: 66150-70573). The file lists consecutive rows with information that reads as follows:
Bld_Shrt_Nrml_BCells_|Femalekontrol|Wh|GM225-01|10RPMormore TCCCCGGCATCTCCACCA (SEQ ID NO: 66150) 371789 14357.5
Bld_ShrtNrml_BCells_|Femalekontrol|Wh|GM22501|10RPMormore TCCCCGGCACCTCCACCA (SEQ ID NO: 66151) 327537 12648.6 (etc.)
where
the first column is a composite string comprising six segments: whether this is a normal ("Bld_Shrt_Nrml_BCells_") or disease ("Bld_Shrt_POAG_BCells") sample; the sex of the individual that provided the sample; whether this is a normal ("control") or disease ("POAG") sample; the race of the patient ("Wh" or "B/Aa"—see above); the sample identifier (e.g., GM22501); and, the minimum RPM threshold used.
the second column lists the number of reads that the corresponding tRF received (e.g., 371789)
the last column lists the normalized abundance of the corresponding tRF in RPM.
2) There are 1316 distinct tRFs that appear with a normalized abundance of ≥10 RPM in at least one of the analyzed datasets: 603 arise from nuclearly-encoded tRNAs and 713 from mitochondrially-encoded tRNAs.
3) There are 530 tRFs that appear with a normalized abundance of ≥10 RPM exclusively in POAG samples but are not present in the control samples: 397 of these 530, or 78.9%, arise from mitochondrial rRNAs. This is particularly notable considering that mitochondrial processes have been linked to POAG.
4) When the 530 tRFs (Table 24) that are exclusive to the POAG samples were compared with the 1866 tRFs that appear with the same level of abundance (i.e., 10 RPM) in the 492 datasets generated from the B-cells of healthy individuals from the 1000 Genomes Project collection (Telonis et al, Oncotarget 2015) only 177 were found in common. This strongly indicates that the same type of cell (in this case a B-cell) produces tRFs in the POAG state that would not be produced by this cell in the "normal" state.
5) When the 530 tRFs that are exclusive to the POAG samples were compared with the 5160 tRFs that appear with the same level of abundance (i.e., 10 RPM)
in one or more of the 10274 datasets from The Cancer Genome Atlas (TCGA)
in one or more of the 492 datasets from the 1000 Genomes Project (see above)

278 of these tRFs were found unique to the POAG samples. This strongly indicates that these tRFs are likely unique to the POAG disease state as they do not seem to be produced by other cell types, normal and diseased. Of these 278 tRFs, 87 were present exclusively in the B/Aa POAG patients, 75 were present exclusively in the Wh POAG patients, and 116 were present in both the B/Aa and Wh POAG patients. Additionally, of these 278 tRFs, 195 or 70.1% arise from mitochondrial tRNAs, a particularly notable result considering that mitochondrial processes have been linked to POAG.

In the CD submitted with the Provisional Patent Application No. 62/498,368, (filed Dec. 22, 2016) Table 24 (ALL_tRNA_seqs.exclusive.transfer_RNAs.10RPMormore. POAG_exclusive.and.NOT_i n_LCL.NOT_in_TC-GA.sequences.txt) lists these 278 sequences (SEQ ID NO: 70574-70851). These tRNA fragment sequences are compelling candidates to serve as blood biomarkers for POAG.

Some tRNA Fragments are Differentially Expressed Between Glaucoma Patients and Controls Datasets Commercially 43 lymphoblastoid cell lines that were generated from the peripheral B lymphocytes of 43 donors after transformation by the Epstein-Barr virus. Of the 43 donors,
10 were B/Aa and affected by primary open angle glaucoma (POAG)—group A1
11 were Wh and affected by POAG—group A2
11 were B/Aa and apparently healthy (served as controls)—group B1
11 were Wh and apparently healthy (served as controls)—group B2 Of note: all 43 donors were selected to be female.

All 43 datasets were deep sequenced. Subsequently, we enumerated the tRFs that arose from each of the 610 nuclear and 22 mitochondrial tRNAs and determined their support in terms of sequenced reads.

Findings

DESeq (Love, Huber and Anders Genome Biology 2014) was used for this analysis, and the following comparisons carried out: A1 vs B1 (i.e. POAG vs. control in B/Aa individuals, Table 54) and A2 vs B2 (i.e. POAG vs. control in Wh individuals, Table 55). Only those rRFs whose abundance ranked them in the top 60%, had a fold change ≥2× and an FDR ≤0.05.

- 228 tRFs were found to be differentially expressed between A1 and B1 (i.e. POAG vs. control in B/Aa individuals). These sequences are listed in Table 54. (SEQ ID NOs: 71359-71586).
- 294 tRFS between A2 and B2 were differentially expressed (i.e. POAG vs. control in Wh individuals). Their sequences are included in table 55, SEQ ID NOs: 71587-71880).

Only 27 of these tRFs were differentially expressed between POAG and controls, in both the Wh and B/Aa individuals.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Lengthy table referenced here

US11578366-20230214-T00001

Please refer to the end of the specification for access instructions.

Lengthy table referenced here

US11578366-20230214-T00002

Please refer to the end of the specification for access instructions.

Lengthy table referenced here

US11578366-20230214-T00003

Please refer to the end of the specification for access instructions.

Lengthy table referenced here

US11578366-20230214-T00004

Please refer to the end of the specification for access instructions.

Lengthy table referenced here

US11578366-20230214-T00005

Please refer to the end of the specification for access instructions.

Lengthy table referenced here

US11578366-20230214-T00006

Please refer to the end of the specification for access instructions.

Lengthy table referenced here

US11578366-20230214-T00007

Please refer to the end of the specification for access instructions.

Lengthy table referenced here

US11578366-20230214-T00008

Please refer to the end of the specification for access instructions.

Lengthy table referenced here

US11578366-20230214-T00009

Please refer to the end of the specification for access instructions.

Lengthy table referenced here

US11578366-20230214-T00010

Please refer to the end of the specification for access instructions.

Lengthy table referenced here

US11578366-20230214-T00011

Please refer to the end of the specification for access instructions.

| Lengthy table referenced here | Lengthy table referenced here |
|---|---|
| US11578366-20230214-T00012 | US11578366-20230214-T00014 |
| Please refer to the end of the specification for access instructions. | Please refer to the end of the specification for access instructions. |

| Lengthy table referenced here | Lengthy table referenced here |
|---|---|
| US11578366-20230214-T00013 | US11578366-20230214-T00015 |
| Please refer to the end of the specification for access instructions. | Please refer to the end of the specification for access instructions. |

LENGTHY TABLES

The patent contains a lengthy table section. A copy of the table is available in electronic form from the USPTO web site (https://seqdata.uspto.gov/?pageRequest=docDetail&DocID=US11578366B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11578366B2). An electronic copy of the "Sequence Listing" will also be available from the USPTO upon request and payment of the fee set forth in 37 CFR 1.19(b)(3).

What is claimed is:

1. A method of treating a female, African American human subject with primary open angle glaucoma, the method comprising:
    isolating fragments of rRNAs from a B-cell sample obtained from the subject; and
    characterizing the rRNA fragments and their relative abundance in the sample by deep sequencing;
    detecting SEQ ID NO: 70890 at a normalized abundance of >10 reads per million relative to control; and
    administering a treatment regimen to the human subject for primary open angle glaucoma.

2. The method of claim 1, wherein isolating the rRNA fragments comprises isolating rRNA fragments with a length in the range of about 15 nucleotides to about 50 nucleotides.

3. The method of claim 1, wherein characterizing the rRNA fragments comprises at least one assessment selected from the group consisting of sequencing the rRNA fragments, measuring overall abundance of one of the rRNA fragments mapped to the genome, measuring a relative abundance of the one rRNA fragment to a reference, assessing a length of the one rRNA fragment, identifying starting and ending points of the one rRNA fragment, identifying genomic origin of the one rRNA fragment, and identifying a terminal modification of the one rRNA fragment.

4. The method according to claim 1, comprising detecting each of SEQ ID NOs: 70951, 71061, 71128, 70919, 71006, 71178, 70890, 70959, 71005, 71284, 70892 and 71113.

5. The method according to claim 1, wherein characterizing the rRNA fragments and their relative abundance in the sample by deep sequencing comprises quantifying abundance levels by dumbbell-PCR.

6. A method of treating a female, African American human subject with primary open angle glaucoma, the method comprising:
    isolating fragments of rRNAs from a B-cell sample obtained from the subject; and
    characterizing the rRNA fragments and their relative abundance in the sample by deep sequencing;
    detecting SEQ ID NO: 70892 at a normalized abundance of >10 reads per million relative to control; and
    administering a treatment regimen to the human subject for primary open angle glaucoma.

7. A method of treating a female, African American human subject with primary open angle glaucoma, the method comprising:
    isolating fragments of rRNAs from a B-cell sample obtained from the subject; and
    characterizing the rRNA fragments and their relative abundance in the sample by deep sequencing;
    detecting SEQ ID NO: 70919 at a normalized abundance of >10 reads per million relative to control; and
    administering a treatment regimen to the human subject for primary open angle glaucoma.

\* \* \* \* \*

UNITED STATES PATENT AND TRADEMARK OFFICE
CERTIFICATE OF CORRECTION

| | | |
|---|---|---|
| PATENT NO. | : 11,578,366 B2 | Page 1 of 1 |
| APPLICATION NO. | : 16/471318 | |
| DATED | : February 14, 2023 | |
| INVENTOR(S) | : Rigoutsos | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this
Seventh Day of January, 2025

Derrick Brent
*Acting Director of the United States Patent and Trademark Office*